US011872205B2

(12) United States Patent
Swiss et al.

(10) Patent No.: US 11,872,205 B2
(45) Date of Patent: *Jan. 16, 2024

(54) METHODS OF TREATING TRIPLE-NEGATIVE BREAST CANCER USING COMPOSITIONS OF ANTIBODIES AND CARRIER PROTEINS

(71) Applicant: Mayo Foundation for Medical Education and Research, Rochester, MN (US)

(72) Inventors: Gerald F. Swiss, Cumming, GA (US); Jesse Crowne, Cumming, GA (US); Svetomir N. Markovic, Rochester, MN (US); Wendy K. Nevala, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/160,036

(22) Filed: Jan. 26, 2023

(65) Prior Publication Data
US 2023/0165828 A1 Jun. 1, 2023

Related U.S. Application Data

(63) Continuation of application No. 16/330,359, filed as application No. PCT/US2017/050134 on Sep. 5, 2017, now Pat. No. 11,590,098.

(60) Provisional application No. 62/383,943, filed on Sep. 6, 2016.

(51) Int. Cl.
*A61K 31/337* (2006.01)
*A61K 47/68* (2017.01)
*A61K 47/69* (2017.01)
*A61K 47/64* (2017.01)
*A61K 47/54* (2017.01)
*A61P 35/00* (2006.01)
*A61K 9/16* (2006.01)

(52) U.S. Cl.
CPC .......... *A61K 31/337* (2013.01); *A61K 9/1658* (2013.01); *A61K 47/549* (2017.08); *A61K 47/643* (2017.08); *A61K 47/6803* (2017.08); *A61K 47/6843* (2017.08); *A61K 47/6845* (2017.08); *A61K 47/6849* (2017.08); *A61K 47/6865* (2017.08); *A61K 47/6869* (2017.08); *A61K 47/6891* (2017.08); *A61K 47/6929* (2017.08); *A61P 35/00* (2018.01)

(58) Field of Classification Search
CPC .................................................. A61K 31/337
See application file for complete search history.

(56) References Cited

U.S. PATENT DOCUMENTS

| | | |
|---|---|---|
| 4,350,687 A | 9/1982 | Lipton et al. |
| 5,026,772 A | 6/1991 | Kobayashi et al. |
| 5,116,944 A | 5/1992 | Sivam et al. |
| 5,216,130 A | 6/1993 | Line et al. |
| 5,252,713 A | 10/1993 | Morgan, Jr. et al. |
| 5,260,308 A | 11/1993 | Poduslo et al. |
| 5,728,541 A | 3/1998 | Kornblith |
| 5,736,137 A | 4/1998 | Anderson et al. |
| 6,054,297 A | 4/2000 | Carter et al. |
| 6,147,060 A | 11/2000 | Zasloff et al. |
| 6,416,967 B2 | 7/2002 | Kornblith |
| 6,537,579 B1 | 3/2003 | Desai et al. |
| 6,933,129 B1 | 8/2005 | Kornblith |
| 7,041,301 B1 | 5/2006 | Markovic |
| 7,112,409 B2 | 9/2006 | Blumenthal et al. |
| 7,678,552 B2 | 3/2010 | Kornblith |
| 7,731,950 B2 | 6/2010 | Noessner et al. |
| 7,758,891 B2 | 7/2010 | Desai et al. |
| 7,820,788 B2 | 10/2010 | Desai et al. |
| 7,906,121 B2 | 3/2011 | Chang et al. |
| 7,923,536 B2 | 4/2011 | Desai et al. |
| 8,034,375 B2 | 10/2011 | Desai et al. |
| 8,119,129 B2 | 2/2012 | Jure-Kunkel et al. |
| 8,138,229 B2 | 3/2012 | Desai et al. |
| 8,268,348 B2 | 9/2012 | Desai et al. |
| 8,314,156 B2 | 11/2012 | Desai et al. |
| 8,344,177 B2 | 1/2013 | Neri et al. |
| 8,735,394 B2 | 5/2014 | Desai et al. |
| 8,853,260 B2 | 10/2014 | Desai et al. |
| 9,101,543 B2 | 8/2015 | Desai et al. |
| 9,387,244 B2 | 7/2016 | Markovic |
| 9,427,477 B2 | 8/2016 | Markovic et al. |
| 9,446,148 B2 | 9/2016 | Markovic et al. |

(Continued)

FOREIGN PATENT DOCUMENTS

| | | |
|---|---|---|
| EP | 1913947 | 4/2008 |
| EP | 3204413 | 8/2017 |

(Continued)

OTHER PUBLICATIONS

Park et al., "Anti-HER2 Immunoliposomes: Enhanced Efficacy Attributable to Targeted Delivery", Clin. Cancer Res., 2002, 8, pp. 1172-1181.
Parker et al., "Targeting CLL Cells Using Rituximab-Conjugated Surface Enhanced Raman Scattering (SERS) Gold Nanoparticles," Blood vol. 116, No. 21, Nov. 1, 2010, pp. 1109.
Perez et al., "Phase 2 Trial of Carboplatin, Weekly Paclitaxel, and Biweekly Bevacizumab in Patients with Unresectable Stage IV Melanoma", Cancer, 2009, vol. 115, Issue 1, pp. 119-127.
Petrelli et al.,"Targeted Delivery for Breast Cancer Therapy: the History of Nanoparticle-Albumin Bound Paclitaxel," Expert Opinion on Pharmacotherapy, Jun. 1, 2010 (Jun. 1, 2010), vol. 11, pp. 1413-1432.

(Continued)

*Primary Examiner* — Benjamin J Packard
(74) *Attorney, Agent, or Firm* — Fish & Richardson P.C.

(57) ABSTRACT

Described herein are methods, formulations and kits for treating a patient with triple-negative breast cancer with nanoparticle complexes comprising a carrier protein (e.g., albumin), paclitaxel and a binding agent specific for a target antigen expressed by the cells (e.g., an anti-VEGF antibody).

20 Claims, No Drawings

(56) References Cited

U.S. PATENT DOCUMENTS

| | | |
|---|---|---|
| 9,533,058 B2 | 1/2017 | Markovic et al. |
| 9,555,128 B2 | 1/2017 | Markovic et al. |
| 9,566,350 B2 | 2/2017 | Markovic et al. |
| 9,757,453 B2 | 9/2017 | Markovic et al. |
| 10,279,035 B2 | 5/2019 | Markovic et al. |
| 10,279,036 B2 | 5/2019 | Markovic et al. |
| 10,300,016 B2 | 5/2019 | Markovic et al. |
| 10,307,482 B2 | 6/2019 | Markovic et al. |
| 10,322,084 B2 | 6/2019 | Markovic et al. |
| 10,376,579 B2 | 8/2019 | Markovic et al. |
| 10,376,580 B2 | 8/2019 | Markovic et al. |
| 10,391,055 B2 | 8/2019 | Markovic et al. |
| 10,406,224 B2 | 9/2019 | Markovic et al. |
| 10,413,606 B2 | 9/2019 | Markovic et al. |
| 10,420,839 B2 | 9/2019 | Markovic et al. |
| 10,441,656 B2 | 10/2019 | Markovic et al. |
| 10,471,145 B2 | 11/2019 | Markovic et al. |
| 10,478,495 B2 | 11/2019 | Markovic et al. |
| 10,493,150 B2 | 12/2019 | Markovic et al. |
| 10,507,243 B2 | 12/2019 | Markovic et al. |
| 10,561,726 B2 | 2/2020 | Swiss et al. |
| 10,596,111 B2 | 3/2020 | Markovic et al. |
| 10,596,112 B2 | 3/2020 | Markovic et al. |
| 10,610,484 B2 | 4/2020 | Markovic et al. |
| 10,618,969 B2 | 4/2020 | Markovic et al. |
| 10,624,846 B2 | 4/2020 | Markovic et al. |
| 10,668,151 B2 | 6/2020 | Markovic et al. |
| 10,765,741 B2 | 9/2020 | Markovic et al. |
| 10,772,833 B2 | 9/2020 | Markovic et al. |
| 10,780,049 B2 | 9/2020 | Markovic et al. |
| 10,780,050 B2 | 9/2020 | Markovic et al. |
| 2002/0111362 A1 | 8/2002 | Rubinfeld |
| 2004/0005318 A1 | 1/2004 | Davis et al. |
| 2004/0077601 A1 | 4/2004 | Adams et al. |
| 2005/0032699 A1 | 2/2005 | Holash et al. |
| 2006/0165652 A1 | 7/2006 | Dudley et al. |
| 2007/0020232 A1 | 1/2007 | Rossignol et al. |
| 2007/0148135 A1 | 6/2007 | Dang et al. |
| 2007/0166388 A1 | 7/2007 | Desai et al. |
| 2009/0004118 A1 | 1/2009 | Nie et al. |
| 2010/0047234 A1 | 2/2010 | Markovic |
| 2010/0092489 A1 | 4/2010 | Van De Winkel et al. |
| 2010/0112077 A1 | 5/2010 | Desai et al. |
| 2010/0172835 A1 | 7/2010 | Ruoslahti et al. |
| 2010/0260679 A1 | 10/2010 | Shachar et al. |
| 2010/0311679 A1 | 12/2010 | Olson et al. |
| 2011/0014117 A1 | 1/2011 | Wang et al. |
| 2011/0076273 A1 | 3/2011 | Adler et al. |
| 2011/0097340 A1 | 4/2011 | Ramachandra et al. |
| 2011/0104143 A1 | 5/2011 | Buchsbaum et al. |
| 2011/0150902 A1 | 6/2011 | Markovic |
| 2011/0262525 A1 | 10/2011 | Wang et al. |
| 2012/0263739 A1 | 10/2012 | Langer et al. |
| 2012/0315273 A1 | 12/2012 | Markovic |
| 2013/0028895 A1 | 1/2013 | Wulf |
| 2013/0071403 A1 | 3/2013 | Rolland et al. |
| 2013/0149238 A1 | 6/2013 | Kavlie et al. |
| 2013/0164816 A1 | 6/2013 | Chang et al. |
| 2014/0056909 A1 | 2/2014 | Markovic |
| 2014/0155344 A1 | 6/2014 | Desai et al. |
| 2014/0161819 A1 | 6/2014 | Hann et al. |
| 2014/0178486 A1 | 6/2014 | Markovic et al. |
| 2014/0302017 A1 | 10/2014 | Markovic |
| 2014/0314774 A1 | 10/2014 | Zhou et al. |
| 2015/0050356 A1 | 2/2015 | Desai et al. |
| 2015/0246122 A1 | 9/2015 | Markovic et al. |
| 2016/0095942 A1 | 4/2016 | Markovic et al. |
| 2016/0184229 A1 | 6/2016 | Markovic et al. |
| 2016/0184452 A1 | 6/2016 | Markovic et al. |
| 2016/0184453 A1 | 6/2016 | Markovic et al. |
| 2016/0235860 A1 | 8/2016 | Markovic et al. |
| 2016/0250351 A1 | 9/2016 | Markovic et al. |
| 2016/0256431 A1 | 9/2016 | Markovic et al. |
| 2016/0263241 A1 | 9/2016 | Markovic et al. |
| 2016/0310610 A1 | 10/2016 | Markovic et al. |
| 2016/0324964 A1 | 11/2016 | Markovic et al. |
| 2016/0338961 A1 | 11/2016 | Markovic et al. |
| 2016/0339118 A1 | 11/2016 | Markovic et al. |
| 2017/0021023 A1 | 1/2017 | Dikstein |
| 2017/0021032 A1 | 1/2017 | Markovic et al. |
| 2017/0021034 A1 | 1/2017 | Markovic et al. |
| 2017/0071897 A1 | 3/2017 | Markovic et al. |
| 2017/0095574 A1 | 4/2017 | Swiss et al. |
| 2017/0100492 A1 | 4/2017 | Markovic et al. |
| 2017/0106087 A1 | 4/2017 | Markovic et al. |
| 2017/0128408 A1 | 5/2017 | Markovic et al. |
| 2017/0128583 A1 | 5/2017 | Markovic et al. |
| 2017/0128584 A1 | 5/2017 | Markovic et al. |
| 2017/0128585 A1 | 5/2017 | Markovic et al. |
| 2017/0128586 A1 | 5/2017 | Markovic et al. |
| 2017/0128587 A1 | 5/2017 | Markovic et al. |
| 2017/0128588 A1 | 5/2017 | Markovic et al. |
| 2017/0182174 A1 | 6/2017 | Markovic et al. |
| 2017/0182175 A1 | 6/2017 | Markovic et al. |
| 2017/0182180 A1 | 6/2017 | Markovic et al. |
| 2017/0182183 A1 | 6/2017 | Markovic et al. |
| 2017/0182184 A1 | 6/2017 | Markovic et al. |
| 2017/0182185 A1 | 6/2017 | Markovic et al. |
| 2017/0182186 A1 | 6/2017 | Markovic et al. |
| 2017/0182187 A1 | 6/2017 | Markovic et al. |
| 2017/0196831 A1 | 7/2017 | Markovic et al. |
| 2017/0196832 A1 | 7/2017 | Markovic et al. |
| 2017/0196833 A1 | 7/2017 | Markovic et al. |
| 2017/0216453 A1 | 8/2017 | Markovic et al. |
| 2017/0232102 A1 | 8/2017 | Markovic et al. |
| 2017/0291952 A1 | 10/2017 | Markovic et al. |
| 2018/0235886 A1 | 8/2018 | Markovic et al. |
| 2019/0022188 A1 | 1/2019 | Markovic |
| 2019/0038761 A1 | 2/2019 | Markovic et al. |
| 2019/0099498 A1 | 4/2019 | Markovic et al. |
| 2019/0184032 A1 | 6/2019 | Markovic et al. |
| 2019/0201546 A1 | 7/2019 | Markovic et al. |
| 2019/0202916 A1 | 7/2019 | Markovic et al. |
| 2019/0216944 A1 | 7/2019 | Markovic et al. |
| 2020/0237907 A1 | 7/2020 | Swiss et al. |
| 2020/0268884 A1 | 8/2020 | Markovic et al. |
| 2020/0308294 A1 | 10/2020 | Markovic et al. |

FOREIGN PATENT DOCUMENTS

| | | |
|---|---|---|
| EP | 3533870 | 9/2019 |
| JP | S60146833 | 8/1985 |
| JP | S6178731 | 4/1986 |
| JP | H04504253 | 7/1992 |
| JP | 2001072589 | 3/2001 |
| JP | 2012522809 | 9/2012 |
| KR | 1020090078330 | 7/2009 |
| RU | 2011/133819 | 2/2013 |
| RU | 2505315 | 1/2014 |
| WO | 89/10398 | 11/1989 |
| WO | 97/49390 | 12/1997 |
| WO | 99/00113 | 1/1999 |
| WO | 99/51248 | 10/1999 |
| WO | 2004/022097 | 3/2004 |
| WO | 2004/096224 | 11/2004 |
| WO | 2006/034455 | 3/2006 |
| WO | 2006/089290 | 8/2006 |
| WO | 2007/027819 | 3/2007 |
| WO | 2007/027941 | 3/2007 |
| WO | 2008/047272 | 4/2008 |
| WO | 2008/057561 | 5/2008 |
| WO | 2008/057562 | 5/2008 |
| WO | 2008076373 | 6/2008 |
| WO | 2008/112987 | 9/2008 |
| WO | 2009/043159 | 4/2009 |
| WO | 2009/055343 | 4/2009 |
| WO | 2010/003057 | 1/2010 |
| WO | 2010/017216 | 2/2010 |
| WO | 2010/118365 | 10/2010 |
| WO | 2010/124009 | 10/2010 |
| WO | 2010/136492 | 12/2010 |
| WO | 2012/048223 | 4/2012 |
| WO | 2012/088388 | 6/2012 |
| WO | 2012/154681 | 11/2012 |

(56) References Cited

FOREIGN PATENT DOCUMENTS

| WO | 2012/154861 | 11/2012 |
|---|---|---|
| WO | 2014/009774 | 1/2014 |
| WO | 2014/037422 | 3/2014 |
| WO | 2014/055415 | 4/2014 |
| WO | 2014/105644 | 7/2014 |
| WO | 2014/123612 | 8/2014 |
| WO | 2015/048520 | 4/2015 |
| WO | 2015/191969 | 12/2015 |
| WO | 2015/195476 | 12/2015 |
| WO | 2016/057554 | 4/2016 |
| WO | 2016/059220 | 4/2016 |
| WO | 2016/089873 | 6/2016 |
| WO | 2017/031368 | 2/2017 |
| WO | 2017/062063 | 4/2017 |
| WO | 2017/120501 | 7/2017 |
| WO | 2017/139698 | 8/2017 |
| WO | 2017/165439 | 9/2017 |
| WO | 2017/165440 | 9/2017 |
| WO | 2017/176265 | 10/2017 |
| WO | 2018/027205 | 2/2018 |
| WO | 2018/045238 | 3/2018 |
| WO | 2018/045239 | 3/2018 |
| WO | 2018/048815 | 3/2018 |
| WO | 2018/048816 | 3/2018 |
| WO | 2018/048958 | 3/2018 |

OTHER PUBLICATIONS

Pikal., "Freeze drying of proteins, Part II: Formulation selection", Biopharm, 1980, 9, pp. 26-30.
Polak et al., "Mechanisms of local immunosuppression in cutaneous melanoma", Br J Cancer, 2007, 96(12), pp. 1879-1887.
Porrata et al., "Early lymphocyte recovery predicts superior survival after autologous hematopoietic stem cell transplantation in multiple myeloma or non-Hodgkin lymphoma", Blood, 2001. 98(3), pp. 579-585.
Porrata et al., "Timely reconstitution of immune competence affects clinical outcome following autologous stem cell transplantation", Clin Exp Med., 2004, 4(2):78-85.
Powell et al., "Adoptive transfer of vaccine-induced peripheral blood mononuclear cells to patients with metastatic melanoma following lymphodepletion", J Immunol., 2006, 177(9), pp. 6527-6539.
Pries et al., "Cytokines in head and neck cancer", Cytokine Growth Factor Rev., 2006, 17(3), pp. 141-146.
Qu Na et al.: "Cabazitaxel-loaded human serum albumin nanoparticles as a therapeutic agent against prostate cancer", International Journal of Nanomedicine, vol. 11. Jul. 26, 2016 (Jul. 26, 2016), pp. 3451-3459.
Ranieri et al., "Vascular endothelial growth factor (VEGF) as a target of bevacizumab in cancer: from the biology to the clinic", Curr. Med. Chem., 2006, 13, 1845-1857.
Rao et al., "Combination of Paclitaxel and Carboplatin as Second-Line Therapy for Patients with Metastatic Melanoma", Cancer, Jan. 15, 2006, vol. 106, No. 2, pp. 375-382.
Ribas et al., "Antitumor activity in melanoma and anti-self responses in a phase I trial with the anti—cytotoxic T lymphocyte-associated antigen 4 monoclonal antibody CP-675,206", J Clin Oncol., Dec. 10, 2005, 23(35), pp. 8968-8977.
Rosenberg et al., "Tumor progression can occur despite the induction of very high levels of self/tumor antigen-specific CD8+ T cells in patients with melanoma", J. Immunol., 2005, 175(9), pp. 6169-6176.
Roy et al., "Tumor associated release of interleukin-10 alters the prolactin receptor and down—regulates prolactin responsiveness of immature cortical thymocytes", J Neuroimmunol., 2007, 186(1-2), pp. 112-120.
Rudikoff et al., "Single amino acid substitution altering antigen-binding specificity," Proc Natl Acad Sci USA 1982 vol. 79 pp. 1979-1983.

Rudnicka et al., "Rituximab causes a polanzation of B cells that augments its therapeutic function in NK-cell-mediated antibody-dependent cellular cytotoxicity", Blood, 2013, 121(23):4694-4702.
Sadat et al., "Nano-pharmaceutical Formulations for Targeted Drug Delivery against HER2 in Breast Cancer", Current Cancer Drug Targets, 2015, 15(1):71-86.
Salven et al., "Enhanced expression of vascular endothelial growth factor in metastatic melanoma", Br. J. Cancer, 1997, 76(7), pp. 930-934.
Samaranayake et al., "Modified taxols. 5.1 Reaction of taxol with electrophilic reagents and preparation of a rearranged taxol derivative with tubulin assembly activity", J. Org. Chem., vol. 56, 1991, pp. 5114-5119.
Sandler et al., "Paclitaxel carboplatin alone or with bevacizumab for non-small-cell lung cancer", N. Engl. J. Med., 2006. 355:2542-2550.
Sato et al., "Intraepithelial CD8+ tumor-infiltrating lymphocytes and a high CD8+/regulatory T cell ratio are associated with favorable prognosis in ovarian cancer", Proc Natl Acad Sci USA, 2005, 102(51):18538-18543.
Schrama et al. "Antibody targeted drugs as cancer therapeutics", Nature Reviews 5:147-159 (2006).
Sester et al., "Differences in CMV-specific T-cell levels and long-term susceptibility to CMV infection after kidney, heart and lung transplantation", Am J Transplant., 5(6):1483-1489, Jun. 2005.
Soda et al., Latest topics of new medicine "Albumin-bound paclitaxel," Mol. Respiratory Dis. 17(1):100-103 (Mar. 1, 2013).
Srivastava et al., "Angiogenesis in cutaneous melanoma: pathogenesis and clinical implications", Microsc Res. Tech., 2003, 60:208-224.
Stancovski et al., "Mechanistic aspects of the opposing effects of monoclonal antivodies to the ER882 receptor on tumor growth," Proc Natl Acad Sci USA, 88. 8691-8695, (1991).
Streit et al., "Angiogenesis, lymphangiogenesis, and melanoma metastasis", Oncogene, 2003, 22, pp. 3172-3179.
Taieb et al., "Chemoimmunotherapy of tumors: Cyclophosphamide synergtizes with exoxome based vaccines", J. Immunol . . . . Mar. 1, 2006, 176(5):2722-2729.
Tao et al., "Inhibiting the growth of malignant melanoma by blocking the expression of vascular endothelial growth factor using an RNA interference approach", Br. J. Dermatol., 2005, 153:715-724.
Tas et al., "Circulating serum levels of angiogenic factors and vascular endothelial growth factor receptors 1 and 2 in melanoma patients", Melanoma Res., 2006, 16:405-411.
Terheyden et al., "Anti-vascular endothelial growth factor antibody bevacizumab in conjunction with chemotherapy in metastasizing melanoma", J Cancer Res Clin Oncol, 2007, 133(11), pp. 897-901.
Terui, English Translation of Molecular-Targeted Therapy for Cancer: Progresses and Challenges, "Daratumurnab. Antibody Drug against Myeloma", Pharma Med., Nov. 10, 2013, vol. 31, No. 11, p. 27-30.
Ugurel et al., "Increased serum concentration of angiogenic factors in malignant melanoma patients correlates with tumor progression and survival"; J. Clin. Oncol., 2001, 19:577-583.
Vacca et al., "Docetaxel versus paclitaxel for antiangiogenesis", J. Hematother. Stem Cell Res., 2002, 11:103-118.
Varker et al., "A randomized phase 2 trial of bevacizumab with or without daily low-dose interferon alfa-2b in metastatic malignant melanoma", Ann Surg Oncol., 14(8):2367-2376, print Aug. 2007, Epub May 2007.
Vence et al., "Circulating tumor antigen-specific regulatory T cells in patients with metastatic melanoma", Proc Natl Acad Sci USA, 2007, 104(52), pp. 20884-20889.
Vishnu et al., "Safety and Efficacy of nab-Paclitaxel in the Treatment of Patients with Breast cancer." Breast Cancer: Basic and Clinical Research. 2011, vol. 5, pp. 53-65.
Volk et al., "Nab-paclitaxel efficacy in the orthotopic model of human breast cancer is significantly enhanced by concurrent anti-vascular endothelial growth factor A therapy," Neoplasia 10(6):613-623 (2008).

(56) References Cited

OTHER PUBLICATIONS

Wagner et al., "Enhanced drug targeting by attachment of an anti alphav integrin antibody to doxorubicin loaded human serum albumin nanoparticles", Biomaterials . . . . 31(8):2388-2398, Epub Dec. 23, 2009.

Walker et al., "Monitoring Immune responses in cancer patients receiving tumor vaccines", Int Rev Immunol., 2003, 22(3-4):283-319.

Wang et al., "Biofunctionalized targeted nanoparticles for therapeutic applications", Expert Opin. Biol. Ther., 2008. 8(8): 1063-1070.

Wang et al., "Paclitaxel at ultra low concentrations inhibits angiogenesis without affecting cellular microtubule assembly", Anti-Cancer Drugs, 2003, vol. 14, Issue 1, pp. 13-19.

Washington University School of Medicine "Phase I/II Study of Abraxane in Recurrent and Refractory Lymphoma", ClinicalTrials.gov, Dec. 6, 2016, 7 pages.

Weber, "Review: anti-CTLA-4 antibody ipilimumab: case studies of clinical response and immune—related adverse events", Oncologist, Jul. 2007, 12(7), pp. 864-872.

Wiernik et al., "Phase I trial of taxol given as a 24-hour infusion every 21 days: responses observed in metastatic melanoma", Journal of Clinical Oncology, Aug. 1987, vol. 5, No. 8, pp. 1232-1239.

Wong et al., "Programmed death-1 blockade enhances expansion and functional capacity of human melanoma antigen-specific CTLs", Int. Immunol., 2007, vol. 19, No. 10, pp. 1223-1234.

Wu et al., "Aptamers: Active Targeting Ligands for Cancer Diagnosis and Therapy", Theranostics, 2015, 5(4):322-344.

Yardley et al., "A pilot study of adjuvant nanoparticle albumin-bound (nab) paclitaxel and cyclophosphamide, with trastuzumab in HER2-positive patients, in the treatment of early-stage breast cancer", Breast Cancer Res Trest, 2010, 123:471-475.

Yee et al., "Adoptive T cell therapy using antigen-specific CD8+ T cell clones for the treatment of patients with metastatic melanoma: in vivo persistence, migration, and antitumor effect of transferred T cells", Proc Natl Acad Sci USA, 2002, 99(25):16168-16173.

Yu et al., "Interaction between bevacizumab and murine VEGF-A: a reassessment," Invest. Ophthalmol. Visual Sci. 49(2): 522-527, Feb. 2008.

Yuan et al., "Vascular Permeability in a Human Tumor Xenograft: Molecular Size Dependence and Cutoff Size", Cancer Research, Sep. 1, 1995, 55, pp. 3752-3756.

Yuan et al., "Time-dependent vascular regression and permeability changes in established human tumor xenografts induced by an and-vascular endothelial growth factor/vascular permeability factor antibody," Proc. Natl. Acad. Sci. USA 93(25):14765-14770 (1996).

Zimpfer-Rechner et al., "Randomized phase IL study of weekly paclitaxel versus paclitaxel and carboplatin as second-line therapy in disseminated melanoma: a multicentre trial of the Dermatologic Co-operative Oncology Group (DeCOG)", Melanoma Res., 2003, 13:531-536.

Anonymous, "Phase I/II Study of Abraxane in Recurrent and Refractory Lymphoma", NCT01555853, ClinicalTrials.gov, Jun. 6, 2014 (8 pages).

U.S. Appl. No. 15/092,403, office action dated May 23, 2019.
U.S. Appl. No. 15/092,433, office action dated May 30, 2019.
U.S. Appl. No. 15/225,428, office action dated Jul. 31, 2019.
U.S. Appl. No. 15/225,542; office action dated Jul. 18, 2019.
U.S. Appl. No. 15/286,024, office action dated Aug. 1, 2019.
U.S. Appl. No. 15/359,569, office action dated Jul. 26, 2019.
U.S. Appl. No. 15/412,581; office action dated Mar. 8, 2019.
U.S. Appl. No. 15/412,610, office action dated Mar. 14, 2019.
U.S. Appl. No. 15/414,526; office action dated Mar. 12, 2019.
U.S. Appl. No. 15/414,533; office action dated Mar. 8, 2019.
U.S. Appl. No. 15/430,411, office action dated May 1, 2019.
U.S. Appl. No. 15/452,669; office action dated Jun. 24, 2019.
U.S. Appl. No. 15/456,377; office action dated Mar. 19, 2019.
U.S. Appl. No. 15/546,377; office action dated Jul. 5, 2019.
U.S. Appl. No. 15/456,382; office action dated Mar. 18, 2019.
U.S. Appl. No. 15/456,382; office action dated Jul. 8, 2019.
U.S. Appl. No. 15/456,391; office action dated Mar. 15, 2019.
U.S. Appl. No. 15/456,391; office action dated Jul. 24, 2019.
U.S. Appl. No. 15/456,395; office action dated Mar. 28, 2019.
U.S. Appl. No. 15/456,395; office action dated Aug. 14, 2019
U.S. Appl. No. 15/450,399; office action dated Mar. 28, 2019.
U.S. Appl. No. 15/456,399; office action dated Aug. 14, 2019.
U.S. Appl. No. 15/460,552; office action dated Apr. 1, 2019.
U.S. Appl. No. 15/460,552; office action dated Aug. 14, 2019.
U.S. Appl. No. 15/460,699; office acton dated Mar. 28, 2019.
U.S. Appl. No. 15/461,288; office action dated Apr. 1, 2019.

Bedu-Addo "Understanding Lyophilization Formulation Development", Pharmaceutical Technology Lyophilization. pp. 10-18 (2004).

Beers et al. "CD20 as a Target for Therapeutic Type I and II Monoclonal Antibodies", Seminars in Hematology 47(2):107-114 (2010).

Belldegrun et al. "Human Renal Carcinoma Line Transfected with Interleukin-2 and/or Interferon alpha Gene(s): Implications for Live Cancer Vaccines", J National Cancer Institute 85(3):207-216 (1993).

Buechner "Intralesional Interferon alfa-2b in the treatment of basal cell carcinoma", J Am Acad Dermatol 24:731-734 (1991).

Cheng et al. Molecularly targeted drugs for metastatic colorectal cancer. Drug Des Deval Ther. Nov. 1, 2013 ;7:1315-22 (Year: 2013).

Coiffier "The Role of Rituximab in Lymphomas", Rev. Bras. Hematol. Hemoter., 2002, vol. 24, No. 3, ISSN: 1516-8484 (6 pages)

Doveil et al. "Adjuvant Therapy of Stage IIIb Melanoma with Interferon Alfa-2b:Clinical and Immunological Relevance", Dermatology 191:234-239 (1995).

Edwards et al. The Remarkable Flexibility of the Human Antibody Repertoire; Isolation of Over One Thousand Different Antibodies to a Single Protein, BLyS', J. Mol. Biol 334:103-118 (2003).

European Application No. 16837869.3, Extended European Search Report dated Apr. 4, 2019.

European Application No. 17736453.6, Extended European Search Report dated Jul. 8, 2019.

International Preliminary Report on Patentability for Application No. PCT/US2017/045643, dated Feb. 14, 2019.

International Preliminary Patentability for Application No. PCT/US2017/049745, dated Mar. 14. 2019.

International Preliminary Report on Patentability for Application No. PCT/US2017/049746, dated Mar. 14, 2019.

International Preliminary Report on Patentability for Application No. PCT/US2017/050137 dated Mar. 21, 2019.

Iqbal et al. Anti-Cancer Actions of Denosumab. Curr Osteoporos Rep. Dec. 2011;9(4): 173-6. (Year 2011).

Khallouf et al. "5-Fluorouracil and Interferon-alpha Immunochemotherapy Enhances Immunogenicity of Murine Pancreatic Cancer Through Upregulation of NKG2D Ligands and MHC Class 1", Immunother 35(3):245-253 (2012).

Korthais et al. "Monocyte derived dendritic cells generated by IFN-alpha acquire mature dendritic and natural killer cell properties as shown by gene expression analysis", J Translated Medicine 5:46 (2007) (11 pages).

Matthey et al. Promising therapeutic targets in neuroblastoma. Clin Cancer Res. May 15, 2012;18(10):2740-53. (Year: 2012).

Package Insert, Campath® (ALEMTUZUMAB), Millennium and ILEX Partners, LP, 13 pages, available May 2001.

Reck et al. "ipilimumab in combination with paclitaxel and carboplatin as first-line therapy in extensive-disease-small-cell lung cancer results from a randomized, double-blind, multicenter phase 2 trial",Ann Oncol. 24(1):75-83 (2013).

Robak, T. Emerging monoclonal antibodies and related agents for the treatment of chronic lymphocytic leukemia. Future Oneal. Jan. 2013;9(1):69-91. Abstract Only. (Year: 2013).

Verma et al. "Effect of surface properties on nanoparticle-cell interactions", Small. 6(1 ): 12-21. (2010).

International Preliminary Report on Patentability for Application No. PCT/US2017/050134 dated Mar. 21, 2019.

Mustacchi et al., "The role of taxanes in triple-negative breast cancer: literature review", Drug Design, Development and Therapy, vol. 9. Aug. 5, 2015, 16 pages.

Hamilton et al., "Nab-Paclitaxel/Bevacizumab/Carboplatin Chemotherapy in First-Line Triple Negative Metastatic Breast Cancer", Clinical Breast Cancer, vol. 13, No. 6, Dec. 1, 2013, 6 pages.

(56) References Cited

OTHER PUBLICATIONS

Nahleh et al., "Swog S0800 (NCI CDR0000636131): addition of bevacizumab to neoadjuvant nab-paclitaxel with dose-dense doxorubicin and cyclophosphamide improves pathologic complete response (pCR) rates in inflammatory or locally advanced breast cancer", Breast Cancer Research and Treatment, vol. 158, No. 3, Jul. 8, 2016, 12 pages.
Adams et al., "Phase Ib trial of atezolizumab in combination with nab-paclitaxel in patients with metastatic triple-negative breast cancer (mTNBC)" Journal of Clinical Oncology vol. 34, No. 15, May 1, 2016, 4 pages.
Fabi et al., "Prospective study on nanoparticle albumin-bound paclitaxel in advanced breast cancer: clinical results and biological observations in taxane-pretreated patients", Drug Design, Development and Therapy, vol. 9, Nov. 1, 2015, 7 pages.
International Search Report and Written Opinion corresponding to International Application No. PCT/US2017/050134 dated Nov. 16, 2017.
International Search Report and Written Opinion corresponding to International Application No. PCT/US2017/050137 dated Nov. 27, 2017.
Anonymous, "Atezolizumab Plus Abraxane Promising New Treatment for Triple-Negative Breast Cancer", UNM Comprehensive Cancer Center, Jan. 7, 2016, pp. 1-2.
Anonymous, "A Phase III, Multicenter, Randomized Placebo-Controlled Study of Atezolizumab (Anti-PD-L1 Antibody) in Combination with Nab Paclitaxel Compared with Placebo with Nab Paclitaxel for Patients with Previously Untreated Metastatic Triple Negative Breast Cancer", ClinicalTrials.gov, Apr. 21, 2015, 1 page.
Elsadek et al., "Impact of albumin on drug delivery—New applications on the horizon", J of Controlled Release, 2011, 1-25.
Elst et al. "Epidermal Growth Factor Receptor Expression and Activity in Acute Myeloid Leukemia", Blood 116:3144 (2010), abstract.
European Application No. 08743903.0, Extended European Search Report dated Jan. 24, 2011.
European Application No. 09774506.1, Extended European Search Report dated Mar. 22, 2012.
European Application No. 12781802.9, Extended European Search Report dated Dec. 18, 2014.
European Application No. 13843209.1, Extended European Search Report dated Sep. 5, 2016.
European Application No. 15806443.6, Extended European Search Report dated Dec. 11, 2017.
European Application No. 15809075.3, Extended European Search Report dated Dec. 21, 2017.
Ferrara et al., "The biology of VEGF and its receptors", Nat. Med., 2003, 9:669-676.
Flaherty et al., "Final Results of E2603: a double-blind, randomized phase III trial comparing carboplatin (C)/ paclitaxel(P) with or without sorafenib(S) in metastatic melanoma", J. Clin Oncol., 2010, 28:15s (suppl: abstr 8511).
Flores et al., "Novel oral taxane therapies: recent Phase I results", Clin. Invest. vol. 3, No. 4, Apr. 1, 2013 (Apr. 1, 2013), pp. 333-341, XP055426571, UK, ISSN: 2041-6792, DOI: 10.4155/cli. 13, 18.
Folkman, "Angiogenesis in cancer, vascular, rheumatoid and other disease", Nat. Med., 1995, 1, 27-31.
Fricke et al., "Vascular endothelial growth factor-trap overcomes defects in dendritic cell differentiation but does not improve antigen-specific immune responses", Clin. Cancer Res., 2007, 13:4840-4848.
Gabrilovich et al., "Production of vascular endothelial growth factor by human tumors inhibits the functional maturation of dendritic cells", Nat. Med., 1996, 2: 1096-1103.
Gao et al., "In vivo cancer targeting and imaging with semiconductor quantum dots", Nat Biotech, 2004, 22(8):969-976.
Gogas et al., "Chemotherapy for metastatic melanoma: time for a change?", Cancer, 2007, 109(3): 455-464.
Golay et al., "Mechanism of action of therapeutic monoclonal antibodies: promises and pitfalls of in vitro and in vivo assay," Arch. Biochem. Biophys. 526(2):146-153 (2012).
Graells et al., Overproduction of VEGF165 concomitantly expressed with its receptors promotes growth and survival of melanoma cells through MAPK and P13K signaling, J. Invest. Dermatol., 2004, 123:1151-1151.
Gupta et al., "Ofatumumab, the first human anti-CD20 monoclonal antibody for the treatment of B cell hematologic malignancies," Ann. N. Y. Acad. Sci., 1263, pp. 43-56 (Jul. 25, 2012).
Haley et al., "Nanoparticles for drug delivery in cancer treatment", Urol. Oncol.: Seminars and Original Invest., 2008, 26:57-64.
Hara, "What is anti-HER2 antibody tubulin polymerization inhibitor complex T-DM1?," Pharm. Monthly 58(5): 734-739 (May 2014).
Harlow et al., Antibodies: A Laboratory Manual, Cold Spring Harbor Laboratory, New York, 1988 (9 pages).
Hassan et al: "Comparison of Different Crosslinking Methods for Preparation of Docetaxel-loaded Albumin Nanoparticles", Iranian Journal of Pharmaceutical Research, vol. 14. No. 2, Apr. 2015 (Apr. 2015), pp. 365-394.
Hauschild et al., "Individualized therapy of disseminated cancer using malignant melanoma as a model", Cancer and Metastasis Reviews, 2006, 25(2): 253-256.
Hauschild et al., "Results of a Phase III, Randomized, Placebo-Controlled Study of Sorafenib in Combination with Carboplatin and Paclitaxel as Second-Line Treatment in Patients with Unresectable Stage III or Stage IV Melanoma", Journal of Clinical Oncology, Jun. 10, 2009, vol. 27, No. 17, pp. 2823-2830.
Hegde et al. "Predictive Impact of Circulating Vascular Endothelial Growth Factor in Four Phase III Trials Evaluating Bevacizumab," Clinical Cancer Research, Feb. 15, 2013 (Feb. 15, 2013) vol. 19, pp. 929-937.
Hersh et al., "A Phase 2 Clinical Trial of nab-Paclitaxel in Previously Treated and Chemotherapy-Naive Patients With Metastatic Melanoma", Cancer, Jan. 1, 2010, 116:155, pp. 155-163.
Hersh et al., "A randomized, controlled phase III trial of nab-Paclitaxel versus dacarbazine in chemotherapy-naïve patients with metastatic melanoma", Ann Oncol, 2015, epub Sep. 26, 2015.
Hersh et al., "Open-label, multicenter, phase II trial of ABI-007 in previously treated and previously untreated patients with metastatic malignant melanoma", J. Clin, Oncol., 2005, 23(16S):7558 (Abstract).
Hobbs et al., "Regulation of Transport pathways in tumor vessels; role of tumor type and microenvironment", Proc Natl Acad Sci USA. Apr. 1998, 95. pp. 4607-4612.
Hodi et al., "Improved survival with ipilimumab in patients with metastatic melanoma", The New England Journal of Medicine, Aug. 19, 2010, vol. 363, No. 8, pp. 711-723.
Hodi et al., "Phase II study of paclitaxel and carboplatin for malignant melanoma", Am. J. Clin. Oncol., 2002, 25:283-286.
Hood et al., Immunology. 1984, Benjamin, N.Y., 2nd edition.
Huncharek et al., "Single-agent DTIC versus combination chemotherapy with or without immunotherapy in metastatic melanoma: a meta-analysis of 3273 patients from 20 randomized trials", Melanoma Research, 11:75-81 (2001).
Hunkapiller et al., "Immunology; The growing immunoglobulin gene superfamily", Nature, Sep. 1986, 323. pp. 15-16.
Huston et al., "Protein engineering of antibody binding sites: Recovery of specific activity in an anti-digoxin single-chain Fv analogue produced in *Escherichia coli*", Proc. Natl. Acad. Sci. USA. Aug. 1988, vol. 85, pp. 5879-5883.
Ibrahim et al.,"Phase I and Pharmacokinetic Study of ABI-007, a Cremophor-free, Protein-stabilized, Nanoparticle Formulation of Paclitaxel", Clinical Cancer Research, May 2002. vol. 8, pp. 1038-1044.
Inagaki et al., "Clinical significance of serum Th1-, Th2—and regulatory T cells-associated cytokines in adult T-cell leukemia/lymphoma: High interleukin-5 and—10 levels are significant unfavorable prognostic factors", Int. J. Cancer. 2006, 118(12):3054-3061.
International Preliminary Report on Patentability for Application No. PCT/US2008/057025, dated Sep. 15, 2009.

(56) References Cited

OTHER PUBLICATIONS

International Preliminary Report on Patentability for Application No. PCT/US2009/049511, dated Jan. 5, 2011.
International Preliminary Report on Patentability for Application No. PCT/US2012/037137, dated Nov. 12, 2013.
International Preliminary Report on Patentability for Application No. PCT/US2013/062638, dated Apr. 16, 2015.
International Preliminary Report on Patentability for Application No. PCT/US2018/035505, dated Dec. 22, 2016.
International Preliminary Report on Patentability for Application No. PCT/US2015/035515, dated Dec. 29, 2016.
International Preliminary Report on Patentability for Application No. PCT/US2015/054295 dated Oct. 13, 2016.
International Preliminary Report on Patentability for Application No. PCT/US2016/026270, dated Oct. 18, 2018.
International Preliminary Report on Patentability for Application No. PCT/US2017/012580, dated Jul. 19, 2018.
International Preliminary Report on Patentability for Application No. PCT/US2017/023442, dated Oct. 4, 2018.
International Preliminary Report on Patentability for Application No. PCT/US2017/023443, dated Oct. 4, 2018.
International Preliminary Report on Patentability for Application PCT/US2016/026267; dated Apr. 10, 2018.
International Preliminary Report on Patentability for Application PCT/US2017/017553, dated Aug. 23, 2018.
International Search Report and Written Opinion for Application No. PCT/US2008/057025, dated Jul. 1, 2008.
International Search Report and Written Opinion for Application No. PCT/US2009/049511, dated Feb. 2, 2010.
International Search Report and Written Opinion for Application No. PCT/US2012/037137, dated Sep. 28, 2012.
International Search Report and Written Opinion for Application No. PCT/US2013/062638, dated Jan. 23, 2014.
International Search Report and Written Opinion for Application No. PCT/US2015/035505, dated Nov. 24, 2015.
International Search Report and Written Opinion for Application No. PCT/US2015/035515, dated Sep. 21, 2015.
International Search Report and Written Opinion for Application No. PCT/US2015/054295, dated Jan. 25, 2016.
International Search Report and Written Opinion for Application No. PCT/US2016/026267, dated Jul. 12, 2016.
International Search Report and Written Opinion for Application No. PCT/US2016/026270, dated Oct. 12, 2017.
International Search Report and Written Opinion for Application No. PCT/US2016/047841, dated Oct. 31, 2016.
International Search Report and Written Opinion for Application No. PCT/US2017/012580, dated Mar. 17. 2017.
International Search Report and Written Opinion for Application No. PCT/US2017/017553, dated Feb. 10, 2017.
International Search Report and Written Opinion for Application No. PCT/US2017/023442, dated Jun. 16, 2017.
International Search Report and Written Opinion for Application No. PCT/US2017/023443, dated Jul. 11, 2017.
International Search Report and Written Opinion for Application No. PCT/US2017/045643, dated Oct. 25, 2017.
International Search Report and Written Opinion for Application No. PCT/US2017/050355 dated Jan. 30, 2018.
Jaime et al., "Paclitaxel antibody conjugates and trehalose for preserving the immunological activity after freeze-drying," Curr Med Chem, 2004, 11(4):439-46 Abstract Only.
Jain et al., "Delivering nanomedicine to solid tumors", Nature Reviews Clinical Oncology, Nov. 2010, 7, pp. 653-664.
Jain et al., "Normalizing tumor vasculature with anti-angiogenic therapy: a new paradigm for combination therapy," Nat. Med. 7(9):987-989 (2001).
Jain, "Normalization of tumor vasculature: an emerging concept in antiangiogenic therapy," Science 307(5706):58-62 (2005).
Jazirehi et al., "Rituximab (anti-CD20) selectively modifies Bcl-xl and apoptosis protease activating factor-1 (Apaf-1) expression and sensitizes human non-Hodgkin's lymphoma B cell lines to paclitaxel-induced apoptosis," Mol. Cancer Ther. 2(11) 1183-93 (2003).
Jiang et al., "Regulation of Immune Responses by T Cells", N Engl J Med., 2006, 354(11): 1166-1176.
Jin et al., "Paclitaxel-loaded nanoparticles decorated with anti-CD133 antibody: a targeted therapy for liver cancer stem cells," J. Nanopart. Res. 2014, 16:2157 (2014).
Jin et al.: "Docetaxel-loaded PEG-albumin nanoparticles with improved antitumor efficiency against non-small cell lung cancer", Oncology Reports vol. 36, No. 2. Aug. 8, 2016 (Aug. 8, 2016), pp. 871-876, XP055425467, ISSN: 1021-335X, DOI: 10.3892/or.2016.4863.
Julien et al. "Utilization of monoclonal antibody-targeted nanomaterials in the treatment of cancer", 2011, MAbs, 3:467-478.
Kamat et al., "Metronomic chemotherapy enhances the efficacy of antivascular therapy in ovarian cancer", Cancer Res., 2007. 67(1):281-288.
Kawai et al., "VEGF121 promotes lymphangiogenesis in the sentinel lymph nodes of non-small cell lung carcinoma patients", Lung Cancer, 2008, 59(1):41-47.
Kelly et al. "Shape-Specific, Monodisperse Nano-Molding of Protein Particles," J. Am. Chem. Soc. 130:5438-5439 (2008).
Kikuchi et al., "Vascular endothelial growth factor and dendritic cells in human squamous cell carcinoma of the oral cavity", Anticancer Res., 2006, 26(3A):1833-1848.
Kim et al., "A dual target-directed agent against interleukin-6 receptor and tumor necrosis factor a ameliorates experimental arthritis", Scientific Rep. 6:20150 (2016).
Kim et al., "BEAM: A Randomized Phase II Study Evaluating the Activity of Bevacizumab in Combination with Carboplatin Plus Paclitaxel in Patients With Previously Untreated Advanced Melanoma", Journal of Clinical Oncoloy: official journal of the American Society of Clinical Oncology, Jan. 1, 2012, vol. 30. No. 1. pp. 34-41.
Kirkwood et al., "A pooled analysis of eastern cooperative oncology group and intergroup trials of adjuvant high-dose interferon for melanoma", Clin Cancer Res., 2004, 10(5):1670-1677.
Kondejewski et al., "Synthesis and characterization of carbohydrate-linked murine monoclonal antibody K20-human serum albumin conjugates", Bioconjug Chern., 5(6):602-611, Nov-Dec. 1994.
Korman et al., "Tumor immunotherapy: preclinical and clinical activity of anti-CTLA4 antibodies", Curr Opin Invest Drugs, 2005, 6(6):582-591.
Kottschade et al., "A Phase II Trial of Nab-Paclitaxel (ABI-007) and Carboplatin in Patients with Unresectable Stage IV Melanoma", Cancer, Apr. 15, 2011, 117(8), pp. 1704-1710.
Kottschade et al., "A Randomized Phase 2 Study of Temozolomide and Bevacizumab or nab-Paclitaxel. Carboplatin, and Bevacizumab in Patients with Unresectable Stage IV Melanoma", Cancer, 2013. vol. 119, Issue 3, pp; 586-592.
Kratz et al., "Serum proteins as drug carriers of anticancer agents: a review", Drug Deliv., 5(4)281-299, 1998.
Kratz, "Albumin as a drug carrier: design of prodrugs, drug conjugates and nanoparticles", J Control Release, 132(3):171-183, Epub May 17, 2008.
Krishnan et al., "Programmed death-1 receptor and interleukin-10 in liver transplant recipients at high risk for late cytomegalovirus disease", Transpl Infect Dis., 12(4):363-70, print Aug. 2010, ePub Jan. 2010.
Kukowska-Latallo et al., "Nanoparticle Targeting of Anticancer Drug Improves Therapeutic Response in Animal Model of Human Epithelial Cancer", Cancer Res, 2005, 65(12):5317-5324.
Kumar et al., Th1/Th2 cytokine imbalance in meningioma, anaplastic astrocytoma and glioblastoma multiforme patients, Oncol. Ren., 2006,15(6):1513-1516.
Lanzavecchia et al., "The use of hybrid hybridomas to target human cytotoxic T lymphocytes", Eur. J. Immunol., 1987, 17, pp. 105-111.
Lau et al.,"Is inhibition of cancer angiogenesis and growth by paclitaxel schedule dependent?", Anti-Cancer Drugs, 2004, 15:871-875.
Lee et al., "The co-delivery of paclitaxel and Herceptin using cationic micellar nanoparticles", Biomaterials vol. 30, No. 5, Feb. 1, 2009, pp. 919-927.

(56) References Cited

OTHER PUBLICATIONS

Lei et al., "Comparing cellular uptake and cytotoxicity of targeted drug carriers in cancer cell lines with different drug resistance mechanisms", Nanomed: Nanotech, Biol, and Med., 2011, 7:324-332.
Lev et al., "Dacarbazine causes transcriptional up-regulation of interleukin 8 and vascular endothelial growth factor in melanoma cells: a possible escape mechanism from chemotherapy", Mol. Cancer Ther., 2003, 2:753-763.
Lev et al., "Exposure of melanoma cells to dacarbazine results in enhanced tumor growth and metastasis in vivo", J. Clin. Oncol., 2004, 22:2092-2100.
Liang et al., "IFN-alpha regulates NK cell cytotoxicity through STAT1 pathway," Cytokine, Aug. 13, 2003 (Aug. 13, 2013), vol. 23. pp. 190-199.
Lin, "Salmon Calcitonin: Conformational Changes and Stabilizer Effects", AIMS Biophysics, 2015, 2(4): 695-723.
Lloyd et al. "Modelling the human Immune response: performance of a 1011 human antibody repertoire against a broad panel of therapeutically relevant antigens", Protein Eng. , Design & Selection 22(3):159-168 (2009).
Lundin et al., "Phase 2 study of alemtuzumab (anti-CD52 monoclonal antibody) in patients with advanced mycosis fungoides/Sezary syndrome", Blood (2003) vol. 101, No. 11, pp. 4267-4272.
Makridis, et al., "MHC class I and II antigen expression and interferon ? treatment of human midgut carcinoid tumors," World Journal of Surgery, Aug. 1, 1993 (Aug. 1, 1993), vol. 16, Iss. 4, pp. 481-486.
Marcoval et al., "Angiogenesis and malignant melanoma, Angiogenesis is related to the development of vertical (tumorigenic) growth phase", J. Cutan. Pathol., 1997, 24:212-218.
Markovic et al., "A phase II study of ABT-510 (thrombospondin-1 analog) for the treatment of metastatic melanoma", Am. J. Clin. Oncol., 2007, 30(3):303-309.
Markovic et al., "A reproducible method for the enumeration of functional ( cytokine producing) versus non-functional peptide-specific cytotoxic T lymphocytes in human peripheral blood", Clin. Exo. Immunol., 2006, 145:438-447.
Markovic et al., "Peptide vaccination of patients with metastatic melanoma: improved clinical outcome in patients demonstrating effective immunization", Am J Clin Oncol., 2006, 29(4):352-360.
Matejtschuk, "Lyophilization of Proteins", Methods in Molecular Biology. Cryopreservation and Freeze-Drying Protocols, Second Edition, Edited by: J.G. Day and G.N. Stacey, Humana Press Inc., Totowa, NJ, 2007, vol. 368, pp. 59-72.
Matsuda et al., Preoperative oral immune-enhancing nutritional supplementation corrects TH1/TH2 imbalance in patients undergoing elective surgery for colorectal cancer, Dis. Colon Rectum, 2006, 49(4):507-516.
Mayo Clinic, "Paclitaxel Albumin-Stabilized Nanoparticles Formulation and Bevacizumab in Treating Patients With Stage IV Melanoma That Cannot Be Removed by Surgery", Dec. 19, 2013, ClinicalTrials.gov., URL: https://www.clinicaltrials.gov/ct2/show/NCT02020707 (Four (4) pages).
McElroy et al., "Imaging of Primary and Metastatic Pancreatic Cancer Using a Fluorophore—Conjugated Anti-CA19-9 Antibody for Surgical Navigation", World J Surg., 2008, 32: 1057-1066.
Meadows et al. "Anti-VEGF Therapies in the Clinic," Cold Spring Harbor Perspectives in Medicine, Oct. 1, 2012 (Oct. 1, 2012). vol. 2. pp. 1-27.
Melcher, "Recommendations for influenza and pneumococcal vaccinations in people receiving chemotherapy", Clin Oncol (R Coll Radion), 2005, 17(1): 12-15.
Merchan et al., "Increased endothelial uptake of paclitaxel as a potential mechanism for its antiangiogenic effects: potentiation by Cox-2 inhibition", Int. J. Cancer, 2005, 113, pp. 490-498.
Mezzaroba et al., "New potential therapeutic approach for the treatment of B-Cell malignancies using chlorambucil/Hydroxychloroquine-Loaded Anti-CD20 Nanoparticles", Sep. 2103, PloS ONE vol. No. 8. Issue 9 pp. 1-10, e74216.
Middleton et al., "Randomized phase III study of temozolomide versus dacarbazine in the treatment of patients with advanced metastatic malignant melanoma", J. Clin. Oncol., 2000, 18, pp. 158-166.
Miller et al., "Paclitaxel plus Bevacizumab versus Paclitaxel Alone for Metastatic Breast Cancer," N Engl. J Med., (2007) vol. 357:2666-2676.
Mimura et al., Vascular endothelial growth factor inhibits the function of human mature dendritic cells mediated by VEGF receptor-2, Cancer Immunol Immunother., 2007, 58(6). pp. 761-770.
Mirtsching et al., "A Phase II Study of Weekly Nanoparticle Albumin-Bound Paclitaxel With or Without Trastuzumab in Metastatic Breast Cancer", Clinical Breast Cancer, 2011, 11(2):121-128.
Mocellin et al., "Cytokines and immune response in the tumor microenvironment"; J Immunother., 2001, 24(5), pp. 392-407.
Motl, "Bevacizumab in combination of chemotherapy for colorectal and other cancers", Am. J. Health-Svst. Pharm 2005, 62, pp. 1021-1032.
Nevala et al, "Abstract 877: Targeted nano-immune conjugates to melanoma: Preclinical testing of bevacizumab targeted nab-paclitaxel", Cancer Immunology Research, vol. 3, Oct. 1, 2015, 3 pages.
Nevala et al, "Antibody-targeted paclitaxel loaded nanoparticles for the treatment of CD20 B-cell lymphoma", Scientific Reports, vol. 7, Apr. 5, 2017, 9 pages.
Nevala et al, "Antibody-Targeted Chemotherapy for the Treatment of Melanoma", Cancer Research, vol. 76, No. 13. Jul. 1, 2016. pp. 3954-3964.
Nevala et al, "Targeted nano-immune conjugates to melanoma: Preclinical testing of bevacizumab targeted nab-paclitaxel", Proceedings of the AACR Special Conference: Tumor Immunology and Immunotherapy: A New Chapter, Dec. 1, 2014, 2 pages.
Ng et al., "Influence of formulation vehicle on metronomic taxane chemotherapy: albumin-bound versus cremaphor EL-based paclitaxel", Clin. Cancer Res., 2006, 12, pp. 4331-4338.
Ng et al., "Taxane-mediated antiangiogenesis in vitro: influence of formulation vehicles and binding proteins", Cancer Res., 2004, 64, pp. 821-824.
Nilvebrant et al., "The Albumin-Binding Domain as a Scaffold for Protein Engineering", Computational and Structural Biotechnology Journal, Mar. 2013, vol. 6. Issue 7, e201303099, http://dx.doi.org/10.5936/csbj.201303099.
Nishida et al, English Translation of "Clinical Trials of New Drugs Cytotoxic Effect against Multiple Myeloma with High Expression of a CD38 Antigen and a Human CD38 Monoclonal Antibody Daratumumab:CD38 Antigen", history of Medicine, Sep. 29, 2012, vol. 242, No. 13, pp. 1176-1181.
Oku et al., "Tumor growth modulation by sense and antisense vascular endothelial growth factor gene expression: effects on angiogenesis, vascular permeability, blood volume, blood flow, fluorodeoxyglucose uptake, and proliferation of human melanoma intracerebral xenografts", Cancer Res., 1998, 58. pp. 4185-4192.
Ortaldo et al., "Effects of several species of human leukocyte interferon on cytotoxic activity o fNK cells and monocytes," International Journal of Cancer, Mar. 15, 1983 (Mar. 15, 1983) vol. 31, No. 3, pp. 285-289.
Ouichi, Antibody delivery—from basics to clinical test—"Clinical development of antibody -drug conjugate," Drug Deliv. Sys. 28(5):424-429 (2013).
Parikh et al., "The vascular endothelial growth factor family and its receptors", Hematol. Oncol. Clin. N. Am., 2004, 18, pp. 951-971.
U.S. Appl. No. 15/752,155; office action dated Dec. 16, 2020.
U.S. Appl. No. 15/430,411, office action dated Nov. 2, 2020.
U.S. Appl. No. 15/452,669; office action dated Oct. 21, 2020.
U.S. Appl. No. 15/456,377; office action dated Sep. 1, 2020.
U.S. Appl. No. 15/675,596; office action dated Oct. 20, 2020.
U.S. Appl. No. 16/086,977; office action dated Sep. 3, 2020.
U.S. Appl. No. 16/330,028; office action dated Nov. 24, 2020.
Molokhia, Sarah A., et al., "The capsule drug device: Novel approach for drug delivery to the eye", Vision Research 50:680-682 (2010).

(56) References Cited

OTHER PUBLICATIONS

Taniwaki, L. et al., "Effect of lyophilization on the in vitro biological activity of bevacizumab", Eye 24: 1628-1629 (Jun. 25, 2010).
U.S. Appl. No. 15/225,542; office action dated Jul. 30, 2020.
U.S. Appl. No. 15/286,024; office action dated Feb. 10, 2020.
U.S. Appl. No. 15/286,024; office action dated Jul. 29, 2020.
U.S. Appl. No. 15/359,569; office action dated Aug. 10, 2020.
U.S. Appl. No. 15/430,411; office action dated Apr. 17, 2020.
U.S. Appl. No. 15/452,669; office action dated Mar. 3, 2020.
U.S. Appl. No. 15/456,377; office action dated Mar. 12, 2020.
U.S. Appl. No. 15/456,391; office action dated Feb. 4, 2020.
U.S. Appl. No. 15/460,699; office action dated Mar. 3, 2020.
U.S. Appl. No. 15/461,283; office action dated Feb. 28, 2020.
U.S. Appl. No. 15/675,596; office action dated May 28, 2020.
U.S. Appl. No. 15/752,155; office action dated Feb. 7, 2020.
U.S. Appl. No. 16/328,146; office action dated Feb. 26, 2020.
U.S. Appl. No. 16/328,146; office action dated Jul. 28, 2020.
Barua et al. "Particle shape enhances specificity of antibody-display nanoparticles", PNAS 110(9):3270-3275 (2013).
Chuang et al. "Recombinant human serum albumin", Drugs Today 43(8):547-561 (2007) (Abstract Only) (2 pages).
European Application No, 17750912.2 Extended European Search Report dated Jan. 2, 2020.
Miele et al. "Albumin-bound formulation of paclitaxel (Abraxane® ABI-007) in the treatment of breast cancer", International Journal of Nanomedicine 4:99-105 (2009).
Warner et al. "Alemtuzumab use in relapsed and refractory chronic lymphocytic leukemia: a history and discussion of future rational use", Ther Adv Hematol 3(6):375-389 (2012).
Zhao et al. "Abraxane, the Nanoparticle Formulation of Paclitaxel Can Induce Drug Resistance by Ip-Regulation of P-gp", PLoS One 10(7):e0131429 (2015) (19 Pages).
Anonymous "Paclitaxel Albumin-Stabilized Nanoparticle Formulation and Bevacizumab in Treating Patients With Stage IV Melanoma That Cannot Be Removed by Surgery or Gynecological Cancers", NCT02020707, ClinicalTrials.gov, Dec. 25, 2013 (13 Pages).
U.S. Appl. No. 15/187,672; office action dated Sep. 11, 2019.
U.S. Appl. No. 15/225,428; office action dated Dec. 6, 2019.
U.S. Appl. No. 15/225,542; office action dated Jan. 14, 2020.
U.A. Appl. No. 15/359,569; office action dated Jan. 17, 2020.
U.S. Appl. No. 15/430,411; office action dated Oct. 31, 2019.
U.S. Appl. No. 15/460,699; office action dated Aug. 28, 2019.
U.S. Appl. No. 15/461,288; office action dated Aug. 28, 2019.
U.S. Appl. No. 15/675,596; office action dated Dec. 3, 2019.
Application No. 151752,155; office action dated Sep. 25, 2019.
Cirstoiu-Hapca et al. "Benefit of anti-HER2-coated paclitaxel-loaded immuno-nanoparticles in the treatment of disseminated ovarian cancer: Therapeutic efficacy and biodistribution in mice", Journal of Controlled Release 144:324-331 (2010).
European Application No. 17771005.0, Extended European Search Report dated Oct. 17, 2019.
European Application No. 17771006.8, Extended European Search Report dated Oct. 10, 2019.
Liu et al. "Freeze-Drying of Proteins", In: Walkers W., Oldenhof H. (eds) Cryopreservation and Freeze-Drying Protocols. Methods in Molecular Biology (Methods and Protocols), vol. 1257, Springer, New York, NY; published online Nov. 14, 2014.
Reynolds et al. "Phase II Trial of Nanoparticle Albumin-Bound Paclitaxel, Carboplatin, and Bevacizumab in First-Line Patients with Advanced Nonsquamous Non-small Cell Lung Cancer", J Thoracic Oncology 4(12):1537-1543 (2009).
"Concurrent Infusions", J Oncol Pract., 4(4): 171. Jul. 2008.
Abraxane® for Injectable Suspension (paclitaxel protein-bound particles for injectable suspension) (albumin-bound), [drug label], 22 pages, Sep. 2009.
Abraxis Bioscience, Inc., "Abraxane: For the adjuvant treatment of node-positive breast cancer administered sequentially to standard doxorubicin-containing combination chemotherapy," Oncologic Drugs Advisory Committee Meeting (available to public Aug. 4, 2006).

Agarwal et al., "Flow Cytometric analysis of Thl and Th2 cytokines in PBMCs as a parameter of immunological dysfunction in patients of Superficial Transitional cell carcinoma of bladder", Cancer Immunol. Immunother., 2006, 55(6):734-743.
Agarwala et al., "Randomized phase III study of paclitaxel plus carboplatin with or without sorafenib as second-line treatment in patients with advanced melanoma", J. Clin. Oncol., 2007, 25(18S):8510 (Abstract).
Allen "Ligand-targeted therapeutics in anticancer therapy, Cancer", Oct. 2002, 2(10), pp. 750-763.
Alley et al., "Contribution of Linker Stability to the Activities of Anticancer Immunoconjugates", Bioconjugate Chem., 2008, 19(3), pp. 759-765.
Anonymous, "A Phase II, multicenter, randomized, double-blind placebo-controlled trial evaluating the efficacy and safety of bevacizumab in combination with carboplatin and paclitaxel chemotherapy for the first-line treatment of patients with metastatic melanoma", U.S. National Institutes of Health, 2007, 3 pages.
Anonymous, "Phase II trial of carboplatin, weekly paclitaxel and biweekly bevacizumab in patients with unresectable stage IV melanoma", U.S. National Institutes of Health, 2007, 4 pages.
Anonymous, "A Study of Bevacizumab With Carboplatin and Paclitaxel Chemotherapy for the First-Line Treatment of Patients With Metastatic Melanoma (BEAM)," ClinicalTrials.gov [online]. Retrieved from the Internet: URL: https://clinicaltrials.gov/archive/NCT00434252/200703 12, dated Mar. 12, 2007, 3 pages.
U.S. Appl. No. 14/116,619; office action dated Feb. 4, 2015.
U.S. Appl. No. 14/116,619; office action dated Apr. 28, 2016.
U.S. Appl. No. 14/116,619; office action dated Sep. 10, 2015.
U.S. Appl. No. 14/432,979; office action dated Jan. 7, 2019.
U.S. Appl. No. 14/432,979; office action dated May 16, 2018.
U.S. Appl. No. 14/432,979; office action dated Jun. 30, 2016.
U.S. Appl. No. 14/432,979; office action dated Oct. 4, 2017.
U.S. Appl. No. 14/432,979; office action dated Dec. 15, 2016.
U.S. Appl. No. 14/882,327; office action dated May 2, 2016.
U.S. Appl. No. 15/030,567; office action dated Sep. 7, 2016.
U.S. Appl. No. 15/030,568; office action dated May 25, 2017.
U.S. Appl. No. 15/030,568; office action dated Jun. 18, 2018.
U.S. Appl. No. 15/030,568; office action dated Dec. 1, 2017.
U.S. Appl. No. 15/052,336; office action dated Jan. 22, 2019.
U.S. Appl. No. 15/052,336; office action dated Feb. 9, 2018.
U.S. Appl. No. 15/052,336; office action dated Sep. 4, 2018.
U.S. Appl. No. 15/052,623; office action dated Jan. 7, 2019.
U.S. Appl. No. 15/052,623; office action dated Feb. 9, 2018.
U.S. Appl. No. 15/052,623; office action dated May 19, 2017.
U.S. Appl. No. 15/052,623: office action dated Jul. 9, 2018.
U.S. Appl. No. 15/052,623; office action dated Nov. 25, 2016.
U.S. Appl. No. 15/060,967; office action dated Aug. 2, 2016.
U.S. Appl. No. 15/064,396; office action dated Aug. 9, 2016.
U.S. Appl. No. 15/092,403; office action dated Apr. 2, 2018.
U.S. Appl. No. 15/092,403; office action dated Oct. 4, 2018.
U.S. Appl. No. 15/092,433; office action dated Mar. 21, 2018.
U.S. Appl. No. 15/092,433; office action dated Aug. 10, 2018.
U.S. Appl. No. 15/092,433; office action dated Oct. 11, 2017.
U.S. Appl. No. 15/092,433; office action dated Dec. 12, 2018.
U.S. Appl. No. 15/187,672; office action dated May 31, 2018.
U.S. Appl. No. 15/187,672; office action dated Nov. 28, 2018.
U.S. Appl. No. 15/202,115; office action dated Jan. 20, 2017.
U.S. Appl. No. 15/202,115; office action dated Sep. 26, 2016.
U.S. Appl. No. 15/225,428; office action dated Aug. 14, 2018.
U.S. Appl. No. 15/225,428; office action dated Dec. 20, 2017.
U.S. Appl. No. 15/225,504; office action dated Apr. 4, 2017.
U.S. Appl. No. 15/225,504; office action dated Aug. 1, 2018.
U.S. Appl. No. 15/225,504; office action dated Nov. 9, 2016.
U.S. Appl. No. 15/225,542; office action dated Apr. 4, 2017.
U.S. Appl. No. 15/225,542; office action dated Nov. 22, 2016.
Adams et al., "(P2-11-01) Safety and clinical activity of atezolizumab (anti-PDL1) in combination with nab-paclitaxel in patients with metastatic triple-negative breast cancer", 2015, XP002775314, 2015 San Antonio Breast Cancer Symposium, URL: http://sabcs.org/portals/sabcs2016/documents/sabcs-2015-abstracts.pdf?v=5.
Emens et al.: "(OT1-01-06) A Phase III randomized trial of atezolizumab in combination with nab-paclitaxel as first line therapy for patients

(56) References Cited

OTHER PUBLICATIONS with metastatic triple-negative breast cancer (mTNBC)", 2015, XP002775313, 2015 San Antonio Breast Cancer Symposium, URL: http://sabcs.org/portals/sabcs2016/documents/sabcs-2015-abstracts.pdf?v=5.
Inman, "Atezolizumab/Nab-Paclitaxel Combo Shows High Response Rates in TNBC", OneLive, Dec. 10, 2015, 4 pages.
International Search Report and Written Opinion corresponding to International Application No. PCT/US2017/049745 dated Dec. 15, 2017.
International Search Report and Written Opinion corresponding to International Application No. PCT/US2017/049746 dated Nov. 27, 2017.
Volk-Draper et al., "Novel Model for Basaloid Triple-negative Breast Cancer: Behavior in Vivo and Response to Therapy", vol. 14, No. 10, Oct. 1, 2012, 18 pages.
U.S. Appl. No. 15/280,005, office action dated Jan. 9, 2017.
U.S. Appl. No. 15/286,006, office action dated Jan. 18, 2018.
U.S. Appl. No. 15/286,006, office action dated May 16, 2017.
U.S. Appl. No. 15/286,024, office action dated Jan. 6, 2017.
U.S. Appl. No. 15/286,024, office action dated May 19, 2017.
U.S. Appl. No. 15/331,754; office action dated Feb. 22, 2019.
U.S. Appl. No. 15/331,754; office action dated Oct. 11, 2018.
U.S. Appl. No. 15/359,569, office action dated Feb. 22, 2017.
U.S. Appl. No. 15/359,569, office action dated Jun. 23, 2017.
U.S. Appl. No. 15/359,569, office action dated Jul. 17, 2018.
U.S. Appl. No. 15/412,536; office action dated Oct. 1, 2018.
U.S. Appl. No. 15/412,554, office action dated Sep. 27, 2018.
U.S. Appl. No. 15/412,564, office action dated Jul. 10, 2018.
U.S. Appl. No. 15/412,581; office action dated Nov. 13, 2018.
U.S. Appl. No. 15/412,596, office action dated Sep. 4, 2018.
U.S. Appl. No. 15/412,596, office action dated Dec. 27, 2018.
U.S. Appl. No. 15/412,610, office action dated Jul. 9, 2018.
U.S. Appl. No. 15/413,257; office action dated Sep. 25, 2018.
U.S. Appl. No. 15/414,526; office action dated Nov. 16, 2018.
U.S. Appl. No. 15/414,533, office action dated Nov. 19, 2018.
U.S. Appl. No. 15/414,536, office action dated Oct. 11, 2018.
U.S. Appl. No. 15/452,669, office action dated May 5, 2017
U.S. Appl. No. 15/452,669, office action dated Nov. 16, 2017.
U.S. Appl. No. 15/452,669, office action dated Nov. 26, 2018.
Arakawa et al., "Protein-Solvent Interactions in Pharmaceutical Formulations", Pharm. Res., Mar 1991, vol. 8, Issue 3, pp. 285-291.
Armitage et al., "New approach to classifying non-Hodgkin's lymphomas: clinical features of the major histologic subtypes. Non-Hodgkin's Lymphoma Classification Project" J Clin Oncol 16, 2780-2795 (1998).
Asadullah et al., "interleukin-10 therapy-review of a new approach", Pharmarcol Rev., 2003, 55(2):241-269.
Atkins et al., "High-dose recombinant interleukin-2 therapy in patients with metastatic melanoma: long-term survival update", Cancer J Sci Am., 2000, Suppl 6:Sil-14.
Atkins. "Interleukin-2. clinical applications", Semin Oncol., 2002, 29(3 Suppl 7):12-27.
Avastin® Bevacizumad, Roche, [drug label], 24 pages, Sep. 2008.
Baba, Olec Science 10(1):15-18 Jan. 2010.
Bairagi et al., Albumin: A Versatile Drug Carrier, Austin Therapeutics. (Nov. 17, 2015) vol. 2. No. 2, p. 1021 (pp. 1-6).
Balch et al., "The new melanoma staging system", Semin Cutan Med Surg., 2003, 22(1):42-54.
Balch et al., "Update on the melanoma staging system; The importance of sentinel node staging and primary tumor mitotic rate", Journal of Surgical Oncology, Aug. 19, 2011, vol. 104, Issue 4, pp. 379-385.
Bauer et al., "Rituximab, ofatumumab, and other monoclonal anti-CD20 antibodies for chronic lymphocytic leukaemia (Review)," Cochrane Database of Systematic Reviews, Issue 11, 125 pages (copyright 2012).
Baumgartner et al., "Melanoma induces Immunosuppression by up-regulating FOXP3(+) regulatory T cells", J Surg Res., 2007, 141(1): 72-77.

Belani et al., "Multicenter, randomized trial for stage IIIB or IV non-small-cell lung cancer using weekly paclitaxel and carboplatin followed by maintenance weekly paclitaxel or observation", J. Clin. Oncol., 2003, 21:2933-2939.
Bird et al., "Single-chain antigen-binding proteins", Science, Oct. 1988, 242(4877), pp. 423-426.
Boasberg et al., "Nab paclitaxel and bevacizumab as first-line therapy in patients with unresectable stage III and IV melanoma", J Clinical Oncology, 2009, 27, No. 15S. abstract #9071.
Boasberg et al., "Phase II trial of nab-paclitaxel and bevacizumab as first-line therapy in patients with unresectable melanoma", Journal of Clinical Oncology, May 20, 2011, vol. 29, No. 15 Supp, 8543.
Bolstad et al., "A comparison of normalization methods for high density oligonucleotide array data based on variance and bias", Bioinformatics, 2003, 19:185-193.
Cao et al., "Response of resistant melanoma to a combination of weekly paclitaxel and bevacizumab", Clin Transl Oncol, 2007, 9:119-120.
Carson et al., "A phase 2 trial of a recombinant humanized monoclonal anti-vascular endothelial growth factor (VEGF) antibody in patients with malignant melanoma", Proceedings of the ASCO vol. 22, No. 2673, General Poster Session, Thirty-Ninth Annual Meeting of the American Society of Clinical Oncology, May 31-Jun. 3, 2003, Chicago, IL., 2 pages.
Celis, "Overlapping human leukocyte antigen class I/II binding peptide vaccine for the treatment of patients with stage IV melanoma: evidence of systemic immune dysfunction", Cancer, 2007, 110(1):203-214.
Chapman et al., "Improved Survival with Vemurafenib in Melanoma with BRAF V600E Mutation", The New England Journal of Medicine. Jun. 30, 2011, vol. 364, Issue 26, pp. 2507-2516.
Chisholm et al., "Response to influenza immunization during treatment for cancer", Arch Dis Child, 2001, 84(6):496-500.
Chong et al., "Combining cancer vaccines with chemotherapy", Expert Opin Pharmacother., 2006, 6(16):2813-2820.
Cleland et al., "The Development of Stable Protein Formulations: A close look at protein aggregation, deamidation, and oxidation", Therapeutic Drug Carrier Systems, 1993, 10(4), pp. 307-377.
Colman, "Effects of amino acid sequence changes on antibody-antigen interactions," Research in Immunology (145(1):33-36, (1994).
Davis, "Affinity separation of antibody-toxin conjugate from albumin-stabilized formulation", Am Biotechnol Lab., 12(4):60-64, Mar. 1994.
Degrasse, "A Single-Stranded DNA Aptamer That Selectively Binds to *Staphylococcus aureus* Enterotoxin B", PLoS One, 2012, 7(3) e33410. pp. 1-7.
Deguchi et al., "Effect of Methotrexate-Monoclonal Anti-Prostatic Acid Phosphatase Antibody Conjugate on Human Prostate Tumor", Cancer Research, Aug. 1986, 46, pp. 3751-3755.
Demirkesen et al., "The correlation of angiogenesis with metastasis in primary cutaneous melanoma: a comparative analysis of microvessel density, expression of vascular endothelial growth factor and basic fibroblastic growth factor", Pathology, 2006, 38:132-137.
Denardo et al., "Inflammation and breast cancer. Balancing immune response: crosstalk between adaptive and innate immune cells during breast cancer progression", Breast Cancer Res., 2007, 9(4):212.
Desai et al., "Enhanced antitumor activity and safety of albumin-bound nab-docetaxel versus polysorbate 80-based docetaxel", Eur. J. Cancer, Suppl.; 18th Symposium on molecular targets and cancer therapeutios; Prague, Czech Republic; Nov. 7-10, 2006, vol. 4. No. 12. Nov. 2006 *Nov.2006), p. 49.
Desai et. al., "Increased antitumor activity, intratumor paclitaxel concentrations, and endothelial cell transport of cremophor-free, albumin-bound paclitaxel, ABI-007, compared with cremophor-based paclitaxel", Clin Cancer Res., 2006, 12(4): 1317-24.
Deweers et al., "Daraturmumab, a novel therapeutic human CD38 monoclonal antibody, induces killing of multiple myeloma and other hematological tumors", J. Immunol., 186(3): 1840-1848, Feb. 1, 2011.
Dudek et al., "Autologous large multivalent immunogen vaccine in patients with metastatic melanoma and renal cell carcinoma", Am. J. Clin. Oncol., Apr. 1, 2008, 31(2):173-181.
Edison, "MorphoSys," 16 pages (Aug. 8, 2013).

(56) References Cited

OTHER PUBLICATIONS

Elbayoumi et al., "Tumor-Targeted Nanomedicines: Enhanced Antitumor Efficacy In vivo of Doxorubicin-Loaded, Long-Circulating Liposomes Modified with Cancer-Specific Monoclonal Antibody", Clin Cancer Res., 2009, 15(6):1973-1980.
Ellyard et al., "Th2-mediated anti-tumour immunity: friend or foe?", Tissue Antigens, 2007, 70(1):1-11.
Communication Pursuant to Article 94(3) EPC European Examination Report for Application Serial No. 17 784 049.3-1111; dated Mar. 13, 2023 (Mar. 13, 2013); 13 pages.
Matsuda Naoko et al.: "Phase II study of panitumumab, nab-paclitaxel, and carboplatin followed by FEC neoadjuvant chemotherapy for patiens with primary HER-2 negative inflammatory breast cancer"; Journal of Clinical Oncology, vol. 33, No. 15_suppl, May 20, 2015 (May 20, 2015), p. 1065, XP093028818.
Matsuda Naoko et al.: "Phase II sutdy of panitumumab, nab-paclitaxel, and carboplatin followed by FEC neoadjuvant chemotherapy for patients with primary HER2-negative inflammatory breast cancer"; Journal of Clinical Oncology, vol. 34, No. 15_suppl, May 20, 2016 (May 20, 2016), p. 1087, XP93028971.
Budhi S. Yadav: "Biomarkers in triple negative breast cancer: A review", World Journal of Clinical Oncology, vol. 6, No. 6, Jan. 1, 2015 (Jan. 1, 2015), XP055577439, 13 pages.
Kalimutho Murugan et al.: "Targeted Therapies for Triple-Negative Breast Cancer: Combating a Stubborn Disease", Trends in Pharmacological Sciences, vol. 36, No. 12, pp. 822-846, XP029339482, 25 pages.

METHODS OF TREATING TRIPLE-NEGATIVE BREAST CANCER USING COMPOSITIONS OF ANTIBODIES AND CARRIER PROTEINS

CROSS REFERENCE TO RELATED APPLICATIONS

This nonprovisional application is a continuation, under 35 U.S.C. § 120, of U.S. patent application Ser. No. 16/330,359 filed on Mar. 4, 2019, which is a 35 U.S.C. § 371 national phase application of PCT Application PCT/US2017/050134 filed Sep. 5, 2017, which claims the benefit of the priority date of U.S. Provisional Application No. 62/383,943, filed Sep. 6, 2016; the entire contents of each of which are incorporated by reference herein in their entireties.

FIELD OF THE INVENTION

This disclosure relates to novel methods and kits for treating triple-negative breast cancer using anti-vascular endothelial growth factor (anti-VEGF) antibodies and carrier protein/VEGF antibody complexes.

BACKGROUND

Breast cancer is the most common malignancy and second leading cause of cancer death among women in the United States, with an estimated 192,370 new cases diagnosed and 40,170 deaths reported in 2009. Among women aged 20 to 59 years, breast cancer remains the leading cause of cancer death despite a steady decrease in breast cancer mortality since 1990. Triple-negative breast cancer (TNBC) is an aggressive clinical phenotype characterized by lack of expression (or minimal expression) of estrogen receptor (ER) and progesterone receptor (PR), as well as an absence of human epidermal growth factor receptor-2 (Her2/neu) overexpression. For example, a 2007 study of more than 50,000 women with breast cancer found that 23% of women with triple-negative breast cancer did not survive past 5 years, versus 7% of women with other types of breast cancer. Unlike patients with ER/PR-positive or HER2-overexpressing cancer, systemic treatment options for patients with TNBC are limited to cytotoxic chemotherapy due to the lack of a molecular target. Despite its chemosensitivity, TNBC is still associated with a poor prognosis. Pal, S. et al. (2011) *Breast Cancer Res Treat.* 125: 627-636.

Thus, there remains a need in the art to improve the efficacy of cancer therapeutics, especially for the treatment of triple-negative breast cancer.

SUMMARY

Disclosed herein are methods for treating a patient afflicted with breast cancer characterized as having a triple negative phenotype, e.g., a breast cancer characterized as estrogen receptor negative, progesterone receptor negative and Her2/neu negative, and further characterized as expressing a target antigen, e.g., VEGF. A method of this invention comprises treating a breast cancer cell characterized as a triple negative phenotype, which method comprises administering to a breast cancer cell characterized as a triple negative phenotype a composition comprising a therapeutic amount of nanoparticle complexes, the complexes comprising: a) a carrier protein; b) an effective amount of a binding agent having an antigen-binding portion that binds to a target antigen expressed by said cancer cells so as to provide directional guidance of the nanoparticle complexes to said cells; and c) an effective amount of paclitaxel. In some embodiments of this invention the binding agent may further comprise a hydrophobic portion. In some embodiments of this invention the hydrophobic portion of the binding agent may be an Fc domain of an antibody. In some embodiments the antigen binding portion maybe an aptamer or a Fab fragment.

The nanoparticle composition useful in the methods disclosed herein may be lyophilized. Upon reconstitution of such lyophilized composition with an aqueous solution, antigen-binding portions of the binding agents are arranged on the outside surface of the nanoparticle complexes and the nanoparticle complexes are capable of binding to the target antigen, e.g., VEGF, in vivo.

In an embodiment of the methods disclosed herein the binding agent is an antibody or fragment thereof.

In an embodiment of this invention the antibody may be an anti-VEGF antibody, e.g., bevacizumab or a biosimilar thereof.

The nanoparticle complexes described herein may comprise paclitaxel in combination with one or more additional chemotherapeutic agents, e.g., a chemotherapeutic agent selected from the group consisting of abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, pazopanib, pemetrexed, picoplatin, romidepsin, satraplatin, sorafenib, vemurafenib, sunitinib, teniposide, triplatin, vinblastine, vinorelbine, vincristine, and cyclophosphamide.

The carrier protein useful in the methods described herein may be, e.g., albumin, gelatin, elastin, gliadin, legumin, zein, a soy protein, a milk protein, and a whey protein. In some embodiments, the carrier protein is albumin. The albumin may be, e.g., human serum albumin or a recombinant human serum albumin. Recombinant human serum albumin is a highly purified and animal-, virus-, and bacteria-free product that was developed as an alternative to plasma-derived human serum albumin.

In one aspect, the nanoparticle complexes useful in the methods described herein contain binding agents, e.g., antibodies, arranged into a substantially single layer on all or part of the surface of the nanoparticle. In an aspect of this invention, each nanoparticle complex comprises between 100 and 1,000 antibodies, e.g., between 400 and 800 antibodies. In some embodiments the average nanoparticle complex size in the composition is from greater than 800 nm to about 3.5 μm. In other embodiments, the average size of the nanoparticle complexes is about 100 nm to less than about 1 micron. In another aspect the average size of the nanoparticle complexes is between about 120 nm to about 800 nm, and between 120 nm and 200 nm. In some embodiments the nanoparticle complex has an average size of about 160 nm. The nanoparticle complex sizes as set forth herein are as measured with light scatter technology using a Mastersizer 2000E (Malvern Instruments Ltd., Worcestershire, England).

In an embodiment, the carrier protein is albumin and the therapeutic agent is paclitaxel, said nanoparticle complexes having an average size of approximately 80 nm to 400 nm, of about 120 nm to about 200 nm, preferably approximately 160 nm.

In an embodiment of the methods of this invention, the patient has not previously been treated with a therapeutic dose of anti-VEGF antibody prior to administration of the nanoparticle composition. In another embodiment, the patient is pretreated with an anti-VEGF antibody prior to administration of the nanoparticle composition. In one embodiment, the anti-VEGF antibody is administered in a sub-therapeutic dose prior to administration of the nanoparticle composition.

In some cases the patient is recalcitrant to conventional hormonal therapies, and/or trastuzumab therapies.

In an embodiment of the methods of this invention, the composition is administered in a dose that provides 75-175 mg/m$^2$ of the paclitaxel to the patient.

In an embodiment, the invention comprises a method for treating a patient afflicted with breast cancer characterized as estrogen receptor negative, progesterone receptor negative and Her2/neu negative and further characterized as expressing VEGF, said method comprises treating said patient with a composition comprising a therapeutic amount of nanoparticle complexes, said complexes comprising: a) human serum albumin; b) bevacizumab or a biosimilar version thereof; and c) paclitaxel.

In an embodiment of the methods of this invention, the ratio of human serum albumin to paclitaxel in the nanoparticles is about 1:1 to about 13:1, about 5:1 to about 9:1, or about 9:1.

In an embodiment of the methods of this invention, the ratio of albumin/paclitaxel to antibody is about 10:1 to about 1:10, or about 5:1 to about 1:5.

DETAILED DESCRIPTION

After reading this description it will become apparent to one skilled in the art how to implement the invention in various alternative embodiments and alternative applications.

However, all the various embodiments of the present invention will not be described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Titles or subtitles may be used in the specification for the convenience of a reader, which are not intended to influence the scope of the present invention.

Throughout this application "VEGF" and "anti-VEGF antibody" are used as examples and it is appreciated that other target antigens, e.g., other cytokines and other chemokines, that are expressed by the triple negative breast cancer cells and other antibodies to such antigens may also be used in the complexes and methods described herein.

Overview

This invention is directed to the treatment of a mammal with breast cancer, characterized as having a triple negative phenotype, e.g., triple-negative breast cancer characterized as estrogen receptor-negative, progesterone receptor-negative and Her2/neu-negative, and is further characterized as expressing a target antigen, e.g., VEGF. A method of this invention comprises treating a breast cancer cell characterized as a triple negative phenotype, which method comprises administering to a breast cancer cell characterized as a triple negative phenotype a composition comprising a therapeutic amount of nanoparticle complexes, the complexes comprising: a) a carrier protein; b) an effective amount of a binding agent having an antigen-binding portion that binds to a target antigen expressed by said cancer cells so as to provide directional guidance of the nanoparticle complexes to said cells; and c) an effective amount of paclitaxel. In some embodiments of this invention the binding agent may further comprise a hydrophobic portion. The hydrophobic portion of the binding agent, may be, e.g., an Fc domain of an antibody.

The methods and materials provided herein can be used to increase the progression-free survival rate in patients with breast cancer, characterized as having a triple negative phenotype. Increasing progression-free survival can improve a patient's quality of life and/or allow breast cancer patients to live longer.

The methods and materials provided herein can be used to increase the overall survival rate in triple breast cancer patients.

As will be apparent to the skilled artisan upon reading this disclosure, the present disclosure relates to methods for treating a patient suffering from triple-negative breast cancer that expresses a target antigen, e.g., VEGF, by treating the patient with a composition comprising a therapeutically effective amount of nanoparticle complexes comprising a carrier protein, e.g., albumin, paclitaxel, and a binding agent that specifically binds to the target antigen (e.g., an anti-VEGF antibody).

The methods also relate to treating a patient suffering from triple-negative breast cancer that comprise cancer cells that expresses a target antigen, e.g., VEGF, with a sub-therapeutic amount of binding agent that specifically binds to the target antigen, (e.g., anti-VEGF antibody) and a composition comprising a therapeutically effective amount of nanoparticle complexes comprising a carrier protein (e.g., albumin), paclitaxel and a binding agent that specifically binds to the target antigen (e.g., anti-VEGF antibody).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Throughout the application "VEGF" and "anti-VEGF antibody" are used in an exemplary fashion and it will be understood that other target antigens, e.g., other cytokines and chemokines, that are expressed by the triple negative breast cancer cells and other antibodies to those antigens may also be used in the complexes and methods described herein.

Definitions

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any sub-range or sub-value there between. Preferably, the term "about" when used with regard to a dose amount means that the dose may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Heretofore, the use of bevacizumab in the treatment of breast cancer was discontinued due to FDA decisions based on the lack of sufficient efficacy of this antibody in this treatment protocol. ABRAXANE®, while approved for metastatic breast cancer treatment, provides an adequate therapy. However, the methods and compositions described herein are contemplated to provide a significantly improved therapy, especially for the difficult-to-treat triple negative breast cancer where mortality rates are unacceptably high. Without being limited to any theory, it is believed the directional guidance provided by the complexation of the antibody in the nanoparticle complexes provides unexpected results.

In view of the foregoing it is contemplated that subtherapeutic amounts of either the chemotherapeutic agent or the antibody may be successfully used in the treatments described herein. As used herein, the term "sub-therapeutic" is used to describe an amount of chemotherapeutic agent or antibody that is below the amount of agent or antibody conventionally used to treat a cancer. For example, a sub-therapeutic amount is an amount less than that defined by the manufacturer as being required for therapy.

The term "nanoparticle" or "nanoparticle complex" as used herein refers to particles having at least one dimension which is less than 5 microns. In preferred embodiments, such as for intravenous administration, the particle is less than 1 micron. For direct administration, e.g., into a tumor, the particle can be larger. Even larger particles are expressly contemplated by the invention.

In a population of particles, the size of individual particles is distributed about a mean. Particle sizes for the population can therefore be represented by an average, and also by percentiles. D50 is the particle size below which 50% of the particles fall. 10% of particles are smaller than the D10 value and 90% of particles are smaller than D90. Where unclear, the "average" size is equivalent to D50. So, for example, AB160 refers to nanoparticles having an average size of 160 nanometers.

The term "nanoparticle" may also encompass discrete multimers of smaller unit nanoparticles. For example, a 320 nm particle may comprise a dimer of a unit 160 nm nanoparticle. For 160 nm nanoparticles, multimers would therefore be approximately 320 nm, 480 nm, 640 nm, 800 nm, 960 nm, 1120 nm, and so on as determined by a Mastersizer 2000 (available from Malvern Instruments Ltd, Worcestershire, UK) as described in PCT/US15/54295.

The term "binding agent" as used herein refers to any compound having an antigen-binding portion specific to an antigen expressed by a cancer cell of interest that binds to said antigen with high specificity, for example having a dissociation constant of $10^{-7}$ M, $10^{-8}$ M, or $10^{-9}$ M or lower. Preferably the dissociation constant is about $10^{-7}$ M to about $10^{-14}$ M. Examples of binding agents that can be effectively employed in the disclosed methods include, but are not limited to, antibodies, such as monoclonal antibodies, e.g., humanized monoclonal antibodies, chimeric antibodies, or polyclonal antibodies, or antigen-binding fragments thereof, as well as aptamers, fusion proteins, and aptamers having or fused to an albumin-binding motif that non-covalently associates with albumin, etc. In an embodiment the binding agent is an exogenous antibody. An exogenous antibody is an antibody not naturally produced in a mammal, e.g., in a human, by the mammalian immune system.

The term "biosimilar" as used herein refers to a biopharmaceutical which is deemed to be comparable in quality, safety, and efficacy to a reference product marketed by an innovator company (see, Section 351(i) of the Public Health Service Act (42 U.S.C. 262(i)).

The term "carrier protein" as used herein refers to proteins that function to transport binding agents and/or therapeutic agents. The binding agents of the present disclosure can reversibly bind to the carrier proteins. Example carrier proteins are discussed in more detail below. Preferably, the carrier protein comprises an antibody-binding motif that non-covalently associates with an antibody.

The term "core" as used herein refers to central or inner portion of the nanoparticle which may be comprised of a carrier protein, a carrier protein and a therapeutic agent, or other agents or combination of agents. In some embodiments, a portion of the binding agent, e.g., an antibody, may be incorporated into the core. In some embodiments, a portion of the binding agent may be associated with (non-covalently bound to) the core.

As used herein, the term "enhancing the therapeutic outcome" and the like relative to a cancer patient refers to a slowing or diminution of the growth of cancer cells or a solid tumor, or a reduction in the total number of cancer cells or total tumor burden.

The term "therapeutic agent" as used herein means an agent which is therapeutically useful, e.g., an agent for the treatment, remission or attenuation of a disease state, physiological condition, symptoms, or etiological factors, or for the evaluation or diagnosis thereof. A therapeutic agent may be a chemotherapeutic agent, for example, mitotic inhibitors, topoisomerase inhibitors, steroids, anti-tumor antibiotics, antimetabolites, alkylating agents, enzymes, proteasome inhibitors, or any combination thereof.

The term "antibody" or "antibodies" as used herein refers to immunoglobulin molecules and immunologically active portions of immunoglobulin molecules (i.e., molecules that contain an antigen binding site that immuno-specifically bind an antigen). The term also refers to antibodies comprised of two immunoglobulin heavy chains and two immunoglobulin light chains as well as a variety of forms including full length antibodies and portions thereof that bind to a target antigen; including, for example, an immunoglobulin molecule, a monoclonal antibody, a chimeric antibody, a CDR-grafted antibody, a humanized antibody, an Fab, an Fab', an F(ab')2, an Fv, a disulfide linked Fv, an scFv, a single domain antibody (dAb), a diabody, a multi-specific antibody, a dual specific antibody, an anti-idiotypic antibody, a bispecific antibody, a functionally active target antigen-binding fragment thereof, bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2nd ed. (1984); Harlow and Lane, Antibodies. A Laboratory Manual, Cold Spring Harbor Laboratory (1988); Hunkapiller and Hood, Nature, 323, 15-16 (1986), which are incorporated herein by reference). The antibody may be of any type (e.g., IgG, IgA, IgM, IgE or IgD). Preferably, the antibody is IgG. An antibody may be non-human (e.g., from mouse, goat, or any other animal), fully human, humanized, or chimeric. In an embodiment the antibody is an exogenous antibody. An exogenous antibody is an antibody not naturally produced in a mammal, e.g., in a human, by the mammalian immune system.

The term "dissociation constant," also referred to as "$K_d$," refers to a quantity expressing the extent to which a particular substance separates into individual components (e.g., the protein carrier, antibody, and optional therapeutic agent).

The terms "lyophilized," "lyophilization" and the like as used herein refer to a process by which the material (e.g., nanoparticle complexes) to be dried is first frozen and then the ice or frozen solvent is removed by sublimation in a vacuum environment. An excipient is optionally included in pre-lyophilized formulations to enhance stability of the lyophilized product upon storage. In some embodiments, the nanoparticle complexes can be formed from individual lyophilized components (carrier protein, antibody, and optional therapeutic agent) prior to use as a therapeutic. In other embodiments, the carrier protein, antibody, and optional therapeutic agent are first combined into nanoparticle complexes and then lyophilized. The lyophilized sample may further contain additional excipients.

The term "buffer" encompasses those agents which maintain the solution pH in an acceptable range prior to lyophilization and may include succinate (sodium or potassium), histidine, phosphate (sodium or potassium), Tris (tris(hydroxymethyl)aminomethane), diethanolamine, citrate (sodium) and the like. The buffer of this invention has a pH in the range from about 5.5 to about 6.5; and preferably has a pH of about 6.0. Examples of buffers that will control the pH in this range include succinate (such as sodium succinate), gluconate, histidine, citrate and other organic acid buffers.

The term "pharmaceutical formulation" refers to preparations which are in such form as to permit the active ingredients to be effective, and which contains no additional components that are toxic to the subjects to which the formulation would be administered.

"Pharmaceutically acceptable" excipients (vehicles, additives) are those which can reasonably be administered to a subject mammal to provide an effective dose of the active ingredient employed.

"Reconstitution time" is the time that is required to rehydrate a lyophilized formulation into a solution.

A "stable" formulation is one in which the protein therein essentially retains its physical stability and/or chemical stability and/or biological activity upon storage.

The term "target molecule" or "target antigen" as used herein refers to any molecule expressed by a cancer cell that is recognized and bound by an antibody, an aptamer, or other binding agent.

Target molecules include, but are not limited to, proteins, peptides, nucleic acids, carbohydrates, lipids, polysaccharides, glycoproteins, hormones, receptors, growth factors, and any portion or fragment of any of the foregoing, e.g., a short amino acid sequence or peptide (optionally glycosylated or otherwise modified) that is specifically bound by a binding agent (e.g., an antibody) or ligand of such target molecule.

The term "treating" or "treatment" covers the treatment of a disease or disorder (e.g., cancer), in a subject, such as a human, and includes: (i) inhibiting a disease or disorder, i.e., arresting its development; (ii) relieving a disease or disorder, i.e., causing regression of the disease or disorder; (iii) slowing progression of the disease or disorder; and/or (iv) inhibiting, relieving, or slowing progression of one or more symptoms of the disease or disorder. In some embodiments "treating" or "treatment" refers to the killing of cancer cells.

The term "kill" with respect to a cancer treatment is directed to include any type of manipulation that will lead to the death of that cancer cell or at least a portion of a population of cancer cells.

The term "dose" refers to an amount of an agent, e.g., the nanoparticle complexes or binding agents described herein, given to a patient in need thereof. The attending clinician will select an appropriate dose of the agent from the range based on, e.g., the patient's weight, age, health, stage of cancer, level of circulating VEGF in the case wherein the agent is an anti-VEGF antibody, and other relevant factors, all of which are well within the skill of the art.

The term "unit dose" refers to a dose of an agent, e.g., the nanoparticle complexes or binding agents described herein, that is given to the patient to provide a desired result. In some instances, the unit dose is sold in a sub-therapeutic formulation (e.g., 10% the therapeutic dose). The unit dose may be administered as a single dose or a series of sub-doses. The therapeutic dose for an agent for a given FDA-approved indication is recited in the prescribing information, for example the therapeutic dose of bevacizumab is 5 mg/kg to 15 mg/kg depending on the condition, and preferably a subtherapeutic dose ranges from 5% to 20% of the therapeutic dose. In a preferred embodiment of this invention such a subtherapeutic dose of an anti-VEGF antibody, e.g., bevacizumab, would range from 0.25 mg/kg to 3 mg/kg, more preferably from 0.5 to 2 mg/kg. The therapeutic dose for an antibody for a given indication where the antibody is not yet FDA approved or the antibody is not yet approved for that indication, will be the amount that correlates to the therapeutic dose that has been approved for other indications, and thus the subtherapeutic dose for the non-FDA approved indications is readily calculated as a percent of the therapeutic dose (e.g., 10% of the therapeutic dose). For example, the therapeutic dose and therefore the subtherapeutic dose of an antibody for the treatment of metastatic breast cancer correlates to the therapeutic dose for metastatic cancers in general that has been approved.

The term "triple-negative breast cancer" refers to a breast cancer characterized as estrogen receptor-negative, progesterone receptor-negative and human epidermal growth factor receptor-2-negative (HER2-negative). The determination of negative status of the estrogen, progesterone, and Her2/neu expression is readily determined by one of skill in the art, e.g., in accordance with the current accepted guidelines. For example, guidelines set forth by the American Society of Clinical Oncology (ASCO) and the College of American Pathologists (CAP) are widely accepted. The ASCO/CAP recommends testing by immunohistochemistry (IHC) or in situ hybridization (ISH) techniques. Further, a cancer is Her2 negative if a single test (or all tests) performed on a tumor specimen show: (a) IHC negative, IHC 1+ or IHC 0, or (b) ISH negative using single-probe ISH or dual-probe ISH. One of skill in the art would recognize that the triple negative cancer described herein does not include any cancer having an apparent histopathologic discordance as observed by the pathologist. Wolff, A C et al. *J Clin Oncol.* 2013 November 1:31(31):3997-4013. Cancer is ER-negative or PR-negative if <1% of tumor cell nuclei are immunoreactive in the presence of evidence that the sample can express ER or PR (positive intrinsic controls are seen). Hammond, E H et al. *J Oncol Pract.* 2010 July; 6(4): 195-197.

Additionally, some terms used in this specification are more specifically defined below.

Nanoparticle Complexes

As described herein, in vitro mixing of nanoparticles comprising a carrier protein and therapeutic agent, e.g., albumin, and paclitaxel (e.g., ABRAXANE®) and a binding agent (e.g., an antibody, e.g., bevacizumab) can result in the formation of macromolecular complexes, the characteristics of which (e.g., size, antibody content, or therapeutic drug content) can be customized depending on need. In some cases, such macromolecular complexes can retain antibody mediated target binding specificity, can retain or exhibit enhanced chemotherapeutic tumor cell cytotoxicity, and can exhibit no additional toxicity beyond that of albumin/therapeutic nanoparticles alone. As also described herein, contacting said carrier protein/therapeutic agent, e.g., paclitaxel, nanoparticles with a binding agent as defined herein, e.g., an anti-VEGF antibody (e.g., bevacizumab) prior to administration to a human (e.g., a triple-negative breast cancer patient) can result in a complex that, when administered as a complex, has an increased ability to treat triple-negative breast cancer as compared to a treatment regimen that includes administering the nanoparticles and the binding agent, e.g., anti-VEGF antibody, separately in a manner that does not form the complexes, e.g., albumin/paclitaxel/anti-VEGF antibody complexes.

Methods for preparing nanoparticles of a carrier protein, e.g., albumin and chemotherapeutics, e.g., paclitaxel, can be found for example in U.S. Pat. Nos. 8,853,260, 7,923,536, 7,820,788, and 6,096,331. ABRAXANE® is available from Celgene Corp. and is a nanoparticle formulation that combines paclitaxel with human albumin.

An anti-VEGF antibody such as bevacizumab is available from Genentech Inc., under the trade name AVASTIN®. Bevacizumab is a recombinant humanized monoclonal IgG1 antibody which contains human framework regions (FRs) and the complementarity-determining regions (CDRs) of a murine antibody that binds to the vascular endothelial growth factor (VEGF). The anti-VEGF antibody fragment, ranibizumab, is available from Genentech Inc., under the trade name LUCENTIS®.

The average diameter of the complexes can be from 0.1 µm to 1 µm. The average diameter of the complexes can be from 0.1 µm to 0.9 µm. The average diameter of the complexes can be from 0.1 µm to 0.5 µm. The average diameter of the complexes can be from 0.1 µm to 0.3 µm. The average diameter of the complexes can be from 0.15 µm to 0.3 µm. The average diameter of the complexes can be from 0.2 µm to 0.8 µm. The average diameter of the complexes can be from 0.2 µm to 0.5 µm. The average diameter of the complexes can be from 0.2 µm to 0.7 µm. The average diameter of the complexes can be from 0.3 µm to 0.5 µm.

In other embodiments, the nanoparticle complexes are larger, e.g., from greater than 800 nm to about 3.5 µm. In some embodiments, the particles are multimers of nanoparticles.

In some embodiments the nanoparticle complexes have average particle sizes of about 160 nm to about 225 nm either freshly made or after lyophilization and resuspension in an aqueous solution suitable for injection.

Preparations of carrier protein (e.g. albumin)/paclitaxel/antibody nanoparticle complexes provided herein, e.g., complexes having an average diameter that is between 1.1 µm and 0.9 µm, can be administered systemically (e.g., intravenously) to treat a breast cancer located within a mammal's body.

Also an aspect of this invention is a method for treating a patient suffering from triple-negative breast cancer which expresses or overexpresses a target molecule, wherein said patient is treated with a composition comprising a therapeutic amount of nanoparticle complexes, the complexes comprising a) a carrier protein; b) an antibody that binds to the target molecule; and c) a therapeutic agent. In some embodiments the target antigen is VEGF. In some embodiments the target antigen is not VEGF, or HER2. Such target antigens are well known in the art depending on the type of cancer and individual phenotypes.

A number of antigens have been found to be associated with TNBC in at least subsets of patients. Non-limiting examples of TNBC-associated antigens include cancer testis (CT) antigens, folate receptor alpha (FR-alpha), programmed death-ligand I (PD-LI), programmed cell death protein I (PD-I), epidermal growth factor receptor (EGFR), C-kit, and basal cytokeratins. CT antigens include those found in the CTDatabase (maintained by the Ludwig Institute for Cancer Research and accessible on the world wide web at cta.lncc.br/index.php). CT antigens of particular interest include, for example and without limitation, TSAGI0, MAGEA family members (e.g., MAGEA2B, MAGEA3, MAGEA4, MAGEA5, MAGEA6, MAGEA9, MAGEA10, MAGEA12), NY-ESO-1/CTAG1B, CTAG2, PLAC1, and DKKL1. Basal cytokeratins include, for example and without limitation, CK-5, CK-14, and CK-17. Antibodies to each of these antigens, as well as any other known TNBC-associated antigens, are expressly contemplated by the present invention.

Anti-PD-LI antibodies include, without limitation, BMS-936559 (made by Bristol-Myers Squibb), atezolizumab (TECENTRIQ®, made by Genentech/Roche), durvalumab (IMFINZI®, AstraZeneca UK Limited), and avelumab (BAVENCIO®, EMD Serono, Inc.).

Anti-PD-I antibodies include, without limitation, nivolumab (OPDIVO®, Bristol-Myers Squibb) or pembrolizumab (KEYTRUDA®, Merck).

Therapeutic agents, in addition to paclitaxel, that are useful in the methods described herein may be any therapeutic agent, e.g., a therapeutic agent selected from the group consisting of abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, pazopanib, pemetrexed, picoplatin, romidepsin, satraplatin, sorafenib, vemurafenib, sunitinib, teniposide, triplatin, vinblastine, vinorelbine, vincristine, and cyclophosphamide.

The carrier protein useful in the methods described herein may be, e.g., albumin, gelatin, elastin, gliadin, legumin, zein, a soy protein, a milk protein, and a whey protein. In some embodiments, the carrier protein is albumin. In other embodiments the albumin is human serum albumin. In other embodiments the albumin is recombinant human serum albumin.

An embodiment of the invention includes a method for increasing the duration of tumor uptake of a chemotherapeutic agent by administering the chemotherapeutic agent in a nanoparticle complex comprising a carrier protein and the chemotherapeutic agent and having surface complexation with an antibody, e.g., an antibody that specifically binds to an antigen on the tumor. The antigen may also be an antigen that is present on and shed by the tumor cell. In some embodiments, the subject receives a subtherapeutic amount of the antibody prior to or concurrently with such nanoparticle complexes.

Carrier protein/paclitaxel/anti-VEGF antibody complexes and methods of preparing the complexes are described, for example, in U.S. Provisional App. No. 62/060,484, filed Oct. 6, 2014; and U.S. Provisional Patent Application Nos. 62/206,770; 62/206,771; and 62/206,772 filed Aug. 18, 2015, as well as PCT Publication No. PCT/US15/54295, filed Oct. 6, 2015. The contents of each of these applications are specifically incorporated by reference in their entireties. Example 1 below provides one example of a detailed protocol for making such complexes.

In some embodiments, the antibodies are a substantially single layer of antibodies on all or part of the surface of the nanoparticle. Preferably, the antibodies associate with (complex with) the albumin via non-covalent bonds. Without being bound by theory, it is contemplated that binding agent interaction with the carrier protein, e.g., complexation of the binding agent to the carrier protein, occurs through an albumin-binding motif on the binding agents and/or an antibody-binding motif on the carrier protein. In one embodiment, the binding agent comprises an albumin-binding motif. In one embodiment, the carrier protein comprises an antibody-binding motif Non-limiting examples of antibody-binding motifs can be found in PCT Application No. PCT/US2017/045643, filed Aug. 4, 2017, which is incorporated herein by reference in its entirety.

Anti-VEGF Antibodies

In some embodiments, the binding agent is an anti-VEGF antibody, e.g., bevacizumab, or a biosimilar version thereof.

Bevacizumab (AVASTIN®, Roche, USA) is a humanized monoclonal antibody that inhibits angiogenesis by blocking the action of vascular endothelial growth factor (VEGF). As such, bevacizumab can slow the growth of new blood vessels in tumors thereby inhibiting the tumors' ability to grow. Bevacizumab has been used to treat various cancers including, non-small cell lung cancer (NSCLC), metastatic colorectal cancer (mCRC), platinum-resistant ovarian cancer (prOC), advanced cervical cancer (CC), metastatic renal cell carcinoma (mRCC), and recurrent glioblastoma (rGBM). Several biosimilar versions of bevacizumab are currently being developed including ABP 215 (Amgen/Allergen, USA), BCD-021 (Biocad, Russia), BI 695502 (Boehringer Ingelheim, Germany), and PF-06439535 (Pfizer, USA), Cizumab (Hetero Drugs, India) among others.

In some embodiments, the sub-therapeutic amount of anti-VEGF antibody is selected from an amount consisting of about 1%, about 5%, about 10%, about 15%, about 20%, about 25%, about 30%, about 35%, about 40%, about 45%, about 50%, about 55% or about 60% of the therapeutic dosage of anti-VEGF antibody. In some embodiments the therapeutic amount of anti-VEGF antibody in the methods of this invention for the treatment of triple-negative breast cancer is 3 mg/kg to 30 mg/kg, 5 mg/kg to 20 mg/kg or 5 mg/kg to 15 mg/kg.

In some embodiments, the sub-therapeutic amount of anti-VEGF antibody is an amount which preferentially blocks circulating VEGF without blocking VEGF associated with tumor.

Treatment Methods

Any appropriate method can be used to administer an albumin-containing nanoparticle/antibody complexes provided herein (e.g., ABRAXANE®/anti-VEGF antibody complexes) to a mammal in need thereof, e.g., a mammal having a triple-negative breast cancer that expresses or over expresses VEGF. For example, a composition containing albumin-containing nanoparticle/antibody complexes such as ABRAXANE®/anti-VEGF polypeptide antibody complexes can be administered via injection (e.g., subcutaneous injection, intramuscular injection, intravenous injection, or intrathecal injection).

In another aspect of the methods of this invention the mammal in need thereof has triple-negative breast cancer and the nanoparticle complexes administered to such mammal comprise an albumin-containing nanoparticle/antibody complex wherein the antibody binds a target molecule on the cancer cell that is not VEGF, e.g., the target molecule may be epidermal growth factor receptor (EGFR) and the anti-EGFR antibody may be Cetuximab/Erbitux; or the target molecule may be the transmembrane glycoprotein NMB (GPNMB), targeted by glembatumumab.

In some cases, the methods and materials provided herein can be used to treat triple-negative breast cancer in any type of mammal including, without limitation, mice, rats, dogs, cats, horses, cows, pigs, monkeys, and humans.

Before administering a composition containing an albumin-containing nanoparticle/antibody complex provided herein (e.g., ABRAXANE®/anti-VEGF antibody complexes) to a mammal, the mammal can be assessed to determine whether or not the mammal has triple-negative breast cancer. Any appropriate method can be used to determine whether or not a mammal has triple-negative breast cancer. For example, a mammal (e.g., human) can be identified as having triple-negative breast cancer using standard diagnostic techniques. In some cases, a tissue biopsy can be collected and analyzed for the amount of estrogen receptor, epidermal growth factor receptor 2, and progesterone receptor expressed by cancer cells by immunohistochemistry or in situ hybridization to determine whether or not a mammal has triple-negative breast cancer.

After identifying a mammal as having triple-negative breast cancer, the mammal can be administered a composition containing carrier protein (e.g.. albumin)/paclitaxel/antibody complexes provided herein (e.g., ABRAXANE®/anti-VEGF antibody complexes). For example, a composition containing ABRAXANE®/anti-VEGF antibody complexes can be administered prior to or in lieu of surgical resection of a tumor. In some cases, a composition containing albumin chemotherapeutic-containing nanoparticle/antibody complexes provided herein (e.g., ABRAX- ANE®/anti-VEGF antibody complexes) can be administered following resection of a tumor.

A composition containing albumin chemotherapeutic-containing nanoparticle/antibody complexes provided herein (e.g., ABRAXANE®/anti-VEGF antibody complexes) can be administered to a mammal in any appropriate amount, at any appropriate frequency, and for any appropriate duration effective to achieve a desired outcome (e.g., to increase progression-free survival). In some cases, a composition containing albumin-containing nanoparticle/antibody complexes provided herein (e.g., ABRAXANE®/anti-VEGF antibody complexes) can be administered to a mammal having triple-negative breast cancer to reduce the progression rate of the breast cancer by 5, 10, 25, 50, 75, 100, or more percent. For example, the progression rate can be reduced such that no additional cancer progression is detected and/or tumor size and/or volume is reduced following treatment. Any appropriate method can be used to determine whether or not the progression rate of breast cancer is reduced. For example, the progression rate of breast cancer can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of cancer (e.g., triple-negative breast cancer) after treatment can be determined and compared to the stage before treatment to determine whether or not the progression rate was reduced. In some cases the overall survival of the subjects is improved.

In general, one aspect of this document features a method for treating a mammal having triple-negative breast cancer. The method comprises, or consists essentially of, administering to the mammal a composition comprising nanoparticle complexes containing albumin and paclitaxel complexed with an anti-VEGF antibody under conditions wherein the length of progression-free survival is increased. The mammal can be a human. The breast cancer can be triple-negative breast cancer. The composition can comprise anti-VEGF antibodies, e.g., bevacizumab, complexed with the nanoparticles. The composition can further comprise an alkylating agent, in some embodiments the alkylating agent is complexed with the nanoparticle complexes. The alkylating agent can be a platinum compound. The platinum compound can be carboplatin. The anti-VEGF antibody can be a humanized antibody. The anti-VEGF antibody can be a chimeric antibody. The anti-VEGF antibody may be bevacizumab or a biosimilar thereof. The composition can be administered by injection. The progression-free survival can be increased by 15 percent. The progression-free survival can be increased by 25 percent. The progression-free survival can be increased by 50 percent. The progression-free survival can be increased by 75 percent. The progression-free survival can be increased by 100 percent. The composition can be administered under conditions wherein the time to progression is increased.

In some cases, a composition containing albumin-containing nanoparticle/antibody complexes provided herein (e.g., ABRAXANE®/anti-VEGF complexes) can be administered to a mammal having triple-negative breast cancer under conditions where progression-free survival is increased (e.g., by 5, 10, 25, 50, 75, 100, or more percent) as compared to the median progression-free survival of corresponding mammals having untreated triple-negative breast cancer or the median progression-free survival of corresponding mammals having triple-negative breast cancer treated with ABRAXANE® and an antibody (e.g., an anti-VEGF antibody) without forming ABRAXANE®/antibody complexes (e.g., without forming ABRAXANE®/anti-VEGF antibody complexes). In some cases, a composition containing albumin-containing nanoparticle/antibody complexes provided herein (e.g., ABRAXANE®/anti-VEGF antibody complexes) can be administered to a mammal having triple-negative breast cancer to increase progression-free survival by 5, 10, 25, 50, 75, 100, or more percent as compared to the median progression-free survival of corresponding mammals having triple-negative breast cancer and having received ABRAXANE® or an antibody (e.g., an anti-VEGF antibody) alone. Progression-free survival can be measured over any length of time (e.g., one month, two months, three months, four months, five months, six months, or longer).

In some cases, a composition containing albumin-containing nanoparticle/antibody complexes provided herein (e.g., ABRAXANE®/anti-VEGF antibody complexes) can be administered to a mammal having triple-negative breast cancer under conditions where the 8-week progression-free survival rate for a population of mammals is 65% or greater (e.g., 66%, 67%, 68%, 69%, 70%, 71%, 72%, 73%, 74%, 75%, 76%, 77%, 78%, 79%, 80% or greater) than that observed in a population of comparable mammals not receiving a composition containing albumin-containing nanoparticle/antibody complexes provided herein (e.g., ABRAXANE®/anti-VEGF antibody complexes). In some cases, a composition containing albumin-containing nanoparticle/antibody complexes provided herein (e.g., ABRAXANE®/anti-VEGF antibody complexes) can be administered to a mammal having triple-negative breast cancer under conditions where the median time to progression for a population of mammals is at least 150 days (e.g., at least 155, 160, 163, 165, or 170 days).

An effective amount of a composition containing albumin-containing nanoparticle/antibody complexes provided herein (e.g., ABRAXANE®/anti-VEGF antibody complexes) can be any amount that reduces the progression rate of triple-negative breast cancer, increases the progression-free survival rate, or increases the median time to progression without producing significant toxicity to the mammal. Typically, an effective amount of ABRAXANE® can be from about 50 mg/m2 to about 260 mg/m2 or about 75-175 mg/m2 or about 80 mg/m2, and an effective amount of an anti-VEGF antibody such as bevacizumab can be from about 3 mg/kg to 30 mg/kg, 5 mg/kg to about 20 mg/kg, or 5 mg/kg to 15 mg/kg (e.g., about 10 mg/kg or 375 mg/m2). If a particular mammal fails to respond to a particular amount, then the amount of ABRAXANE® or anti-VEGF antibody 20 can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application, which factors are routinely considered by those of skill in the art in determining the effective amount. For example, the frequency of administration, duration of treatment, use of multiple treatment agents, route of administration, and severity of the triple-negative breast cancer may require an increase or decrease in the actual effective amount administered. The complexes may comprise 100-1000 antibodies, e.g., about 400 to about 800 antibodies.

The frequency of administration can be any frequency that reduces the progression rate of triple-negative breast cancer, increases the progression-free survival rate, or increases the median time to progression without producing significant toxicity to the mammal. For example, the frequency of administration can be from about once a month to about three times a month, or from about twice a month to about six times a month, or from about once every two months to about three times every two months. The frequency of administration can remain constant or can be variable during the duration of treatment. A course of treatment with a composition containing ABRAXANE®/anti-VEGF antibody complexes can include rest periods. For example, a composition containing ABRAXANE®/anti-VEGF antibody complexes can be administered over a two week period followed by a two week rest period, and such a regimen can be repeated multiple times. As with the effective amount, those of skill in the art in determining the frequency of administration routinely consider various factors that can influence the actual frequency of administration used for a particular application. For example, the effective amount, duration of treatment, use of multiple treatment agents, route of administration, and severity of the triple-negative breast cancer may require an increase or decrease in administration frequency.

An effective duration for administering a composition provided herein can be any duration that reduces the progression rate of triple-negative breast cancer, increases the progression-free survival rate, or increases the median time to progression without producing significant toxicity to the mammal. Thus, the effective duration can vary from several days to several weeks, months, or years. In general, the effective duration for the treatment of triple-negative breast cancer can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the triple-negative breast cancer.

A composition containing albumin-chemotherapeutic agent-containing nanoparticle/antibody complexes provided herein (e.g., ABRAXANE®/anti-VEGF antibody complexes) can be in any appropriate form. For example, a composition provided herein may be lyophilized or can be in the form of a solution or powder with or without a diluent to make an injectable suspension. A composition also can contain additional ingredients including, without limitation, pharmaceutically acceptable vehicles. A pharmaceutically acceptable vehicle can be, for example, saline, water, lactic acid, mannitol, or combinations thereof.

Co-Treatment Methods Using Antibodies and Nanoparticle Complexes

In one aspect is provided a method for treating a patient suffering from triple-negative breast cancer which expresses VEGF wherein said patient is co-treated with a sub-therapeutic amount of an anti-VEGF antibody and a composition comprising a nanoparticle complex comprising a) a carrier protein (e.g. albumin). b) an effective amount an anti-VEGF antibody) so as to provide directional guidance to the nanoparticle comples, and c) effective amount of paclitaxel, such that the administration of the sub-therapeutic amount of the anti-VEGF antibody enhances the efficacy of the nanoparticle complexes.

In one embodiment, the sub-therapeutic amount of anti-VEGF antibody is selected from an amount consisting of about 1%, about 5%, about 1 0%, about 15%, about 20%, about 25%, about 30%, about 35%, about 40%, about 45%, about 50%, about 55% or about 60% of the therapeutic dosage of anti-VEGF antibody. It is contemplated that administration of the sub-therapeutic amount of anti-VEGF antibody preferentially blocks circulating VEGF with minimal blocking of VEGF associated with a tumor. In some embodiments, the sub-therapeutic amount of anti-VEGF to be administered to the patient is determined by analyzing the level of circulating VEGF in the blood.

For the sake of clarification, "co-treatment" refers to treatment of the triple-negative breast cancer expressing VEGF (a soluble cytokine) with an anti-VEGF antibody prior to, concurrently with, or immediately after administration of the albumin/paclitaxel/anti-VEGF antibody nanoparticle complex, provided that the anti-VEGF antibody is capable of preferentially binding soluble VEGF.

In some embodiments the anti-VEGF antibody is administered prior to the albumin-bound chemotherapeutic/anti-VEGF antibody complex, for example, the anti-VEGF antibody can be administered minutes, hours or days prior to administration of the albumin/paclitaxel/anti-VEGF antibody nanoparticle complex. In some embodiments, the anti-VEGF antibody is administered between about 5 to about 59 minutes, about 10 to about 50 minutes, about 15 to about 45 minutes, about 20 to about 40 minutes, about 25 to about 35 minutes prior to administration of the albumin/paclitaxel/anti-VEGF antibody complex. In other embodiments, the anti-VEGF antibody can be administered about 1 hour, about 2 hours, about 3 hours, about 4 hours, about 5 hours, about 6 hours, about 12 hours, about 24 hours, about 48 hours, about 72 hours, or longer prior to administration of the albumin/paclitaxel/anti-VEGF antibody complex. In other embodiments, the anti-VEGF antibody can be administered about 1 day, about 2 days, about 3 days, about 4 days, about 5 days, about 6 days, about 7 days, about 10 days, about 12 days, about 15 days, or longer prior to administration of the albumin/paclitaxel/anti-VEGF antibody complex.

In some embodiments, the anti-VEGF antibody can be administered concurrently with administration of the albumin/paclitaxel/anti-VEGF antibody complex, for example, within 10 minutes or less of each other.

In other embodiments, the anti-VEGF antibody can be administered subsequent to administration of the albumin/paclitaxel/anti-VEGF antibody complex, for example, within 2 hours after administration of the albumin/paclitaxel/anti-VEGF antibody complex, provided that the subsequent administration allows the antibody to preferentially bind the soluble VEGF.

In one embodiment, the anti-VEGF antibody is administered in a sub-therapeutic dose prior to administering the nanoparticle complex. In this embodiment, the administration of the anti-VEGF antibody occurs about 0.5 to 48 hours prior to administration of the nanoparticle complexes.

In another embodiment, the anti-VEGF antibody is administered between 0.5 hours prior to and up to 0.5 hours after administration of the nanoparticle complexes. In this embodiment, it is contemplated that such administration will nevertheless result in binding of some of the circulating VEGF by the antibody.

Also an aspect of this invention is a method for treating a patient suffering from triple-negative breast cancer that expresses or overexpresses a target antigen (e.g., VEGF or a target antigen other than VEGF) that is in the blood stream, wherein said patient is treated with a sub-therapeutic amount of an antibody that binds to the target antigen and a composition comprising nanoparticle complexes, the complexes comprising a) a carrier protein; b) an antibody that binds to the target antigen, e.g., anti-VEGF antibodies; and c) paclitaxel, such that the administration of said sub-therapeutic amount of the antibody enhances the efficacy of said nanoparticle complexes. Further, without wishing to be bound by any theory, it is contemplated that administration of a sub-therapeutic amount of the antibody alone prior to, concurrently with, or after administration of the nanoparticle complexes enhances the efficacy of the nanoparticle complexes. Without wishing to be bound by theory it is contemplated that the antibody alone binds to target antigens naturally expressed in the body and not bound to the tumor, e.g., soluble VEGF. Treatment with a sub-therapeutic amount of the antibody may allow for greater targeting of the nanoparticle complexes to the tumor, thereby decreasing the amounts of the albumin/paclitaxel/antibody complexes administered to a patient needed to achieve the effect achieved by the complexes without pre-treatment, or both.

In another aspect, provided herein are methods for enhancing the efficacy of albumin/paclitaxel/anti-VEGF antibody nanoparticle complexes by administering the albumin/paclitaxel/anti-VEGF antibody nanoparticle complexes about 0.5 to 48 hours after pretreatment of a patient with a sub-therapeutic amount of anti-VEGF antibody.

Preferably, such nanoparticle complexes are administered about 24 hours after the sub-therapeutic amount of anti-VEGF antibody.

In another aspect, provided herein are methods for enhancing the therapeutic outcome in a patient suffering from triple-negative breast cancer expressing soluble VEGF. The patient selected is treated with nanoparticle complexes comprising albumin, paclitaxel and anti-VEGF antibodies, which method comprises treating said patient with a sub-therapeutic amount of said anti-VEGF antibody prior to any subsequent treatment with the nanoparticle complexes. In some embodiments, said antibodies of the nanoparticle complexes are integrated onto and/or into said nanoparticle complexes.

In another aspect, provided herein are methods for enhancing the therapeutic outcome in a patient suffering from triple-negative breast cancer overexpressing soluble VEGF, said method comprising treating the patient with a sub-therapeutic amount of said anti-VEGF antibody and co-treating said patients with an effective amount of nanoparticle complexes comprising albumin-bound paclitaxel and anti-VEGF antibodies. In some embodiments, said antibodies of the nanoparticle complexes are integrated onto and/or into said nanoparticle complexes.

In yet another embodiment, the antibody composition can be administered up to 2 hours post administration of the nanoparticle complexes.

In another aspect, there are provided methods for enhancing the efficacy of albumin/paclitaxel/anti-VEGF antibody nanoparticle complexes by administering the albumin//paclitaxel/anti-VEGF antibody nanoparticle complexes about 0.5 to 48 hours after pretreatment of a patient with a sub-therapeutic amount of anti-VEGF antibody. Preferably, such nanoparticle complexes are administered about 24 hours after administration of a sub-therapeutic amount of anti-VEGF antibody.

In another aspect, there are provided methods for enhancing the therapeutic outcome in a patient suffering from triple-negative breast cancer expressing soluble VEGF which patient is selected to be treated with nanoparticle complexes comprising albumin-bound paclitaxel and anti-VEGF antibodies, which method comprises treating the patient with a sub-therapeutic amount of the anti-VEGF antibody prior to any subsequent treatment with the nanoparticle complexes.

In another aspect, there are provided methods for enhancing the therapeutic outcome in a patient suffering from triple-negative breast cancer overexpressing soluble VEGF, said method comprising treating the patient with a sub-therapeutic amount of said anti-VEGF antibody and co-treating said patients with an effective amount of nanoparticle complexes comprising albumin-bound paclitaxel and anti-VEGF antibodies. In some embodiments, said antibodies of the nanoparticle complexes are integrated onto and/or into said complexes.

In another aspect, there is provided a method for enhancing the therapeutic outcome in a patient suffering from triple-negative breast cancer expressing soluble VEGF, which patient is to be treated with nanoparticle complexes comprising albumin-bound paclitaxel and anti-VEGF antibodies, the method comprises treating said patient with a sub-therapeutic amount of said anti-VEGF antibody within +/−0.5 hours of administration of said nanoparticle complexes.

In another aspect is provided a method for enhancing the therapeutic outcome in a patient suffering from triple-negative breast cancer overexpressing soluble VEGF which patient has been treated with a sub-therapeutic amount of said anti-VEGF antibody, said method comprising treating said patients with an effective amount of nanoparticles complexes comprising albumin-bound paclitaxel and anti-VEGF antibodies within 0.5 hours of administration of said antibodies.

After administering a composition provided herein to a mammal, the mammal can be monitored to determine whether or not the composition provided beneficial results. For example, the mammal can be assessed after treatment to determine whether or not the progression rate of triple-negative breast cancer was reduced (e.g., stopped) or survival rate has increased. As described herein, any method can be used to assess progression and survival rates.

Formulations—Antibodies

In one aspect, the anti-VEGF is a unit-dose formulation of an anti-VEGF antibody which formulation comprises from about 1% to about 60% of a therapeutic dose of said antibody wherein said formulation is packaged so as to be administered as a unit dose. In an aspect of the invention, the unit-dose formulation of an anti-VEGF antibody comprises about 10% of a therapeutic dose of said antibody. For example 10% of a therapeutic dose of an anti-VEGF antibody, e.g., bevacizumab, may be 0.5 mg/kg to 5 mg/kg.

In some embodiments, the formulation comprises from about 5% to about 20% of a therapeutic dose of bevacizumab or a biosimilar version thereof. The therapeutic dose for bevacizumab for a given approved indication, e.g., treatment for metastatic colorectal cancer, non-squamous non-small cell lung cancer, metastatic breast cancer, glioblastoma, and metastatic renal cell carcinoma, is recited in the prescribing information. In each case the therapeutic dose is from 5 to 15 mg/kg and preferably a subtherapeutic dose ranges from 5% to 20% of the therapeutic dose. In such a preferred embodiment such a subtherapeutic dose would range from 0.25 mg/kg to 3 mg/kg, more preferably from 0.5 to 2 mg/kg.

The unit-dose formulation of an anti-VEGF antibody can be about 1% to about 60%, about 5% to about 50%, about 10% to about 40%, about 15% to about 30%, about 20% to about 25%, of a therapeutic dose of the anti-VEGF antibody. Contemplated values include any value, sub-range, or range within any of the recited ranges, including endpoints.

In some embodiments, the anti-VEGF antibody is bevacizumab or a biosimilar version thereof, which formulation comprises from about 5% to about 20% of a therapeutic dose of bevacizumab or a biosimilar version thereof.

In another aspect, provided herein is a formulation comprising an anti-VEGF antibody provided herein, and at least one pharmaceutically acceptable excipient.

In general, the unit-dose formulations provided herein can be formulated for administration to a patient by any of the accepted modes of administration. Various formulations and drug delivery systems are available in the art. See, e.g., Remington's Pharmaceutical Sciences, edited by E. W. Martin (Mack Publishing Company, 18$^{th}$ ed., 1995) and Remington: The Science and Practice of Pharmacy, edited by Allen, Loyd V., Jr, 22$^{nd}$ edition (2012).

In general, unit-dose formulations provided herein will be administered as pharmaceutical compositions by any one of the following routes: oral, systemic (e.g., transdermal, intranasal or by suppository), or parenteral (e.g., intramuscular, intravenous or subcutaneous) administration.

The unit-dose formulations may be comprised of, in general, an anti-VEGF antibody, optionally in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

In other aspects, provided herein are unit-dose formulations of an anti-VEGF antibody, for example, bevacizumab or a biosimilar version thereof which formulation comprises from about 1% to about 60% of a therapeutic dose of said antibody wherein said formulation is packaged so as to be administered as a unit dose.

Formulations—Compositions Comprising Nanoparticle Complexes

In one aspect, the compositions comprising the nanoparticle complexes described herein are formulated for systemic delivery, e.g., intravenous administration.

In one aspect, the nanoparticle composition is formulated for direct injection into a tumor. Direct injection includes injection into or proximal to a tumor site, perfusion into a tumor, and the like. Because the nanoparticle composition is not administered systemically, a nanoparticle composition that is formulated for direct injection into a tumor may comprise any average particle size. Without being bound by theory, it is believed that larger particles (e.g., greater than 500 nm, greater than 1 µm, and the like) are more likely to be immobilized within the tumor, thereby providing what is believed to be a better beneficial effect.

In another aspect, provided herein is a composition comprising a compound provided herein, and at least one pharmaceutically acceptable excipient.

In general, the compounds provided herein can be formulated for administration to a patient by any of the accepted modes of administration. Various formulations and drug delivery systems are available in the art. See, e.g., Gennaro, A. R., ed. (2012) Remington's Pharmaceutical Sciences, 18$^{th}$ ed., Mack Publishing Co. (1995) and Remington: The Science and Practice of Pharmacy, edited by Allen, Loyd V., Jr, 22$^{nd}$ edition (2012).

In general, compounds provided herein will be administered as pharmaceutical compositions by any one of the following routes: oral, systemic (e.g., transdermal, intranasal or by suppository), or parenteral (e.g., intramuscular, intravenous or subcutaneous) administration.

The compositions are comprised of, in general, a compound of the present invention in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 18$^{nd}$ ed., 1995) and Remington: The Science and Practice of Pharmacy, edited by Allen, Loyd V., Jr, 22$^{nd}$ edition (2012).

The present formulations of antibody or composition comprising nanoparticle complexes may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising antibodies or nanoparticle complexes as described herein formulated in a compatible pharmaceutical carrier may also be prepared, placed in an appropriate container, and labeled for treatment of an indicated condition.

Kits

In some aspects, the current invention relates to kits comprising: (a) an amount of an albumin/paclitaxel/anti-VEGF antibody complexes, (b) a unit dose of a sub-therapeutic amount of anti-VEGF antibody, and optionally (c) instructions for use.

In some embodiments, the kits can include lyophilized complexes of the albumin/paclitaxel/anti-VEGF antibody.

In some preferred embodiments, the kit components can be configured in such a way that the components are accessed in their order of use. For example, in some aspects the kit can be configured such that upon opening or being accessed by a user, the first component available is the unit dose of a sub-therapeutic amount of anti-VEGF antibody, for example, in a first vial. A second container (e.g., a vial) comprising or containing an amount of the albumin/paclitaxel/anti-VEGF antibody complexes can then be accessed. As such, the kits can be intuitively configured in a way such that the first vial must be opened prior to the second vial being opened. It should be understood that in some embodiments, the order can be different, for example, where it is desired to administer the complex first, prior to the administration of the antibody. Also, it can be configured such that both are administered at the same time. Finally, it should be understood that additional vials or containers of either or both component(s) can be included, and configured for opening in any desired order. For example, the first vial could be antibody, the second vial could include complex, a third could include an antibody or complex, etc. It is contemplated that a kit configured in such a way would prevent, or at least help to prevent, the components from being administered in an order not intended by the instructions for use.

In some aspects, the invention is directed to a kit of parts for administration of albumin-bound chemotherapeutic/anti-VEGF antibody complexes and a unit dose of a sub-therapeutic amount of anti-VEGF antibody; and optionally further comprising a dosing treatment schedule in a readable medium. In some embodiments, the dosing schedule includes the sub-therapeutic amount of anti-VEGF antibody required to achieve a desired average serum level is provided. In some embodiments, the kit of parts includes a dosing schedule that provides an attending clinician the ability to select a dosing regimen of the sub-therapeutic amount of anti-VEGF antibody based on the sex of the patient, mass of the patient, and the serum level that the clinician desires to achieve. In some embodiments, the dosing treatment is based on the level of circulating VEGF in the blood of the patient. In some embodiments, the dosing schedule further provides information corresponding to the volume of blood in a patient based upon weight (or mass) and sex of the patient. In an embodiment, the storage medium can include an accompanying pamphlet or similar written information that accompanies the unit dose form in the kit. In an embodiment, the storage medium can include electronic, optical, or other data storage, such as a non-volatile memory, for example, to store a digitally-encoded machine-readable representation of such information.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

EXAMPLES

The present disclosure is illustrated by administering to a subject in need thereof, e.g., a patient having a triple-negative breast cancer that also expresses VEGF, a composition comprising a therapeutically effective amount of nanoparticle complexes composed of albumin-bound paclitaxel (i.e., ABRAXANE®) and bevacizumab (i.e., AVASTIN®).

The present disclosure is also illustrated by pretreating a subject in need thereof, e.g., a patient having a triple-negative breast cancer that also expresses VEGF, with bevacizumab (i.e., AVASTIN®) followed by administering to the subject a composition comprising a therapeutically effective amount of nanoparticle complexes composed of albumin-bound paclitaxel (i.e., ABRAXANE®) and bevacizumab (i.e.,)AVASTIN®.

One skilled in the art would understand that making and using the nanoparticle complexes, as well as administration of a co-treatment of bevacizumab, of the Examples are for the sole purpose of illustration, and that the present disclosure is not limited by this illustration.

Any abbreviation used herein, has normal scientific meaning. All temperatures are ° C. unless otherwise stated. Herein, the following terms have the following meanings unless otherwise defined:

| | |
|---|---|
| ABX = | ABRAXANE ®/(albumin-bound paclitaxel) |
| ADC = | antibody dependent chemotherapy |
| BEV = | bevacizumab |
| BSA = | bovine serum albumin |
| $dH_2O$ = | distilled water |
| kg = | kilogram |
| nm = | nano molar |
| mg = | milligram |
| ml or mL = | milliliter |
| $m^2$ = | square meters |
| $mm^3$ = | cubic millimeter |
| µg = | microgram |
| µl = | microliter |
| µm = | micrometer/micron |
| PBS = | Phosphate buffered saline |

Example 1: Nanoparticle Complex Preparation

ABRAXANE® (ABX) (10 mg) is suspended in bevacizumab (BEV) (4 mg [160 µl] unless otherwise indicated), and 840 µl of 0.9% saline is added to give a final concentration of 10 mg/ml and 2 mg/ml of ABX and BEV, respectively. The mixture is incubated for 30 minutes at room temperature (or at the temperature indicated) to allow particle formation. For Mastersizer experiments to measure particle size of ABX:BEV complexes, 10 mg of ABX is suspended in BEV at concentrations of 0 to 25 mg/ml. Complexes of ABX with rituximab (0-10 mg/ml) or trastuzumab (0-22 mg/ml) were formed under similar conditions.

For use in humans, the ABX:BEV complexes may be prepared by obtaining the dose appropriate number of 4 mL vials of 25 mg/mL BEV and diluting each vial per the following directions to 4 mg/mL. The dose appropriate number of 100 mg vials of ABX can be prepared by reconstituting to a final concentration containing 10 mg/mL ABX nanoparticles. Using a sterile 3 mL syringe, 1.6 mL (40 mg) of bevacizumab (25 mg/mL) can be withdrawn and slowly injected, over a minimum of 1 minute, onto the inside wall of each of the vials containing 100 mg of ABX. The bevacizumab solution should not be injected directly onto the lyophilized cake as this will result in foaming. Then, using a sterile 12 mL sterile syringe, 8.4 mL 0.9% Sodium Chloride Injection, USP, can be withdrawn and slowly injected, over a minimum of 1 minute, 8.4 mL onto the inside wall of each vial containing ABX 100 mg and BEV 40 mg. Once the addition of BEV 1.6 mL and 0.9% Sodium Chloride Injection, USP 8.4 mL is completed, each vial can be gently swirled and/or inverted slowly for at least 2 minutes until complete dissolution of any cake/powder occurs. Generation of foam should be avoided. At this point, the concentration of each vial should be 100 mg/IO mL ABX and 40 mg/IO mL BEV. The vials containing the ABX and BEV should sit for 60 minutes. The vial(s) should be gently swirled and/or inverted every 10 minutes to continue to mix the complex. After 60 minutes has elapsed, the calculated dosing volume of ABX and BEV should be withdrawn from each vial and slowly added to an empty viaflex bag. An equal volume of 0.9% Sodium Chloride Injection, USP is then added to make the final concentration of ABX 5 mg/mL and BEV 2 mg/mL. The bag should then be gently swirled and/or inverted slowly for 1 minute to mix. The ABX:BEV nanoparticles can be stored for up to 4 hours at room temperature following final dilution.

Example 2: Treatment of Triple-Negative Breast Cancer with ABX/BEV Complexes Reduces Tumor Size Athymic nude mice are injected with 2 to 4×10$^6$ triple-negative breast cancer cells in the right flank and PBS, 12 mg/kg BEV, 30 mg/kg ABX, or AB160, is administered to the mice, or 1.2 mg/kg BEV is administered to the mice and, 24 hr. later, AB160 is administered to the mice. AB160 is prepared as described in PCT Application No. PCT/US15/54295 and Example 1 above. The tumor size is tracked over 40 days. Data is represented as tumor volume in mm3. Only mice treated with AB160 (with or without pretreatment with BEV) show a reduction in average tumor volume.

It is expected that pretreatment with a subtherapeutic dose of anti-VEGF antibodies (BEV) improves the efficacy of the AB160 nanoparticle complexes. Without wishing to be bound by theory, pretreatment with a subtherapeutic amount of BEV may clear systemic levels of VEGF, leaving a greater relative concentration of VEGF at the tumor such that tumor-associated VEGF targeting by the AB160 nanoparticles is more effective.

Tumors are measured on day 15 following treatment with either saline (PBS), AVASTIN® (BEV), ABRAXANE® (ABX), AB160, or a pretreatment of BEV one day before AB160 (BEV+AB160). A 10% sub-therapeutic dose of BEV, as compared to the dose give to the BEV alone or AB160 cohort, is given to the BEV+AB160 cohort 24 hours prior to administration of the AB160. Pretreatment with BEV+AB160, will increase survival. Both treatment groups will have substantially greater survival than the PBS, BEV-only or ABX-only treatment groups. Survival is again assessed at day 40.

Example 3: Fluorescence Over Time of AlexaFluor 750 Labeled Nanoparticles

Mice receive IV injections of equal amounts of either labeled ABRAXANE®, or nanoparticles of ABRAXANE® having surface complexation with bevacizumab (BEV) as per Example 1 above (AB160); one AB160 group of mice receive a pretreatment 1.2 mg/kg of bevacizumab. Fluorescent imagery is done at an excitation/emission spectrum of 710/760. Regions of interest (ROI) in the mice are assigned by software to track tumor accumulation based on a fluorescence threshold. Fluorescence per unit area of background ROIs and tumor ROIs for all three treatment groups are determined at 24, 29, and 48 hours post injection Pretreatment with BEV will result in higher levels of tumor fluorescence as compared to AB160 alone or ABRAXANE alone. Pretreatment with BEV and use of ABRAXANE® nanoparticles having surface complexation with BEV provides for a method for increasing the duration of tumor uptake of albumin containing a chemotherapeutic agent both at 24 hours and 48 hours. Without being limited to any theory, the antibody coating of the albumin nanoparticles imparts stability possibly by reducing liver or kidney clearance and/or by reducing protease degradation of the albumin carrier. This approach allows targeting antibodies to complex with a protein carrier such as albumin thereby providing prolonged targeting of such antibody-bound complexes to the tumor.

Example 4: Nanoparticles Having a Size of 225 nm

To make a nanoparticle having a size of 225 nm, the particles are prepared in accordance with Example 1 but the ratio of BEV to ABRAXANE® was 4:5, i.e., 4 parts BEV and 5 parts ABRAXANE. This ratio produced nanoparticles having a size of 225 nm (AB225). The effect of AB225 is assayed in animals as set forth above. The survival of the mice treated with a single dose of saline, BEV24 (24 mg/kg), ABX30(30 mg/kg), AB160 (12 mg/kg BEV and 30 mg/kg ABX) and AB225 (24 mg/kg BEV and 30 mg/kg ABX) and with AB160 with a BEV (1.2 mg/kg) pretreatment is determined at 30 days.

What is claimed is:

1. A method for treating a patient afflicted with breast cancer characterized as having a triple negative phenotype and further characterized as expressing an antigen, said method comprises administering to the patient a therapeutic amount of nanoparticle complexes, said nanoparticle complexes comprising: a) albumin; b) an effective amount of a binding agent having an antigen-binding portion that binds to the antigen so as to provide directional guidance of the nanoparticle complexes to said cancer; and c) an effective amount of paclitaxel; wherein the average size of the nanoparticle complexes is from about 100 nm to about 3.5 µm.

2. The method of claim 1, wherein said binding agents are arranged on the outside surface of the nanoparticle complexes.

3. The method of claim 1, wherein the binding agent is an antibody selected from an anti-VEGF antibody, an anti-cancer testis (CT) antigen antibody, an anti-folate receptor alpha (FR-alpha) antibody, an anti-programmed death-ligand 1 (PD-L1) antibody, an anti-programmed cell death protein 1 (PD-1) antibody, an anti-epidermal growth factor receptor (EGFR) antibody, an anti-C-kit antibody, and an anti-basal cytokeratin antibody.

4. The method of claim 3, wherein the binding agent is the anti-VEGF antibody, and wherein the anti-VEGF antibody is bevacizumab or a biosimilar version thereof.

5. The method of claim 3, wherein the binding agent is an anti-CT antigen antibody.

6. The method of claim 5, wherein the CT antigen is selected from TSAG10, a MAGE family member, NY-ESO-1/CTAG1B, CTAG2, PLAC1, and DKKL1.

7. The method of claim 6, wherein the MAGE family member is selected from MAGEA2B, MAGEA3, MAGEA4, MAGEA5, MAGEA6, MAGEA9, MAGEA10, and MAGEA12.

8. The method of claim 3, wherein the binding agent is an anti-basal cytokeratin antibody.

9. The method of claim 8, wherein the anti-basal cytokeratin antibody is an anti-CK-5 basal cytokeratin antibody, an anti-CK-14 basal cytokeratin antibody, or an anti-CK-17 basal cytokeratin antibody.

10. The method of claim 3, wherein the binding agent is the anti-PD-L1 antibody, and wherein the anti-PD-L1 antibody is BMS-936559, atezolizumab, durvalumab, or avelumab.

11. The method of claim 3, wherein the binding agent is the anti-PD-1 antibody, and wherein the anti-PD-1 antibody is nivolumab or pembrolizumab.

12. The method of claim 3, wherein the binding agent is the anti-EGFR antibody, and wherein the anti-EGFR antibody is cetuximab or panitumumab.

13. The method of claim 1, wherein the albumin is human serum albumin.

14. The method of claim 13, wherein the albumin is recombinant human serum albumin.

15. The method of claim 1, wherein each nanoparticle complex comprises between 100 and 1,000 antibodies.

16. The method of claim 1, wherein the binding agents are arranged into a substantially single layer of antibodies on all or part of a surface of the nanoparticle complexes.

17. The method of claim 1, wherein the average size of nanoparticle complexes is from about 800 nm to about 3.5 µm.

18. The method of claim 1, wherein the average size of the nanoparticle complexes is from about 100 nm to about 1 micron.

19. The method of claim 1, wherein said nanoparticle complexes have an average size of approximately 160 nm.

20. The method of claim 1, wherein the cancer cell has not previously been treated with an anti-VEGF antibody.

\* \* \* \* \*